(12) United States Patent
Bagwell et al.

(10) Patent No.: US 10,219,832 B2
(45) Date of Patent: Mar. 5, 2019

(54) DEVICE AND METHOD FOR LESS FORCEFUL TISSUE PUNCTURE

(71) Applicant: Actuated Medical, Inc., Bellefonte, PA (US)

(72) Inventors: Roger B. Bagwell, Bellefonte, PA (US); Ryan S. Clement, State College, PA (US); Andrew J. Meehan, Warriors Mark, PA (US); Casey A. Scruggs, Middleburg, PA (US); Ryan M. Sheehan, Pittsburgh, PA (US); Maureen L. Mulvihill, Bellefonte, PA (US)

(73) Assignee: Actuated Medical, Inc., Bellefonte, PA (US)

(*) Notice: Subject to any disclaimer, the term of this patent is extended or adjusted under 35 U.S.C. 154(b) by 493 days.

(21) Appl. No.: 14/522,681

(22) Filed: Oct. 24, 2014

(65) Prior Publication Data

US 2015/0073357 A1 Mar. 12, 2015

Related U.S. Application Data

(63) Continuation-in-part of application No. 14/329,177, filed on Jul. 11, 2014, which is a continuation of
(Continued)

(51) Int. Cl.
*A61B 17/34* (2006.01)
*A61M 5/315* (2006.01)
(Continued)

(52) U.S. Cl.
CPC ........ *A61B 17/3476* (2013.01); *A61B 10/025* (2013.01); *A61B 17/3401* (2013.01);
(Continued)

(58) Field of Classification Search
CPC ........ A61B 17/320068; A61B 5/4887–5/4896; A61B 2017/00115; A61B 17/3476;
(Continued)

(56) References Cited

U.S. PATENT DOCUMENTS

| 4,428,748 A | 1/1984 | Peyman |
| 4,553,541 A | 11/1985 | Burns |

(Continued)

FOREIGN PATENT DOCUMENTS

| EP | 0266058 | 5/1988 |
| EP | 1647255 | 4/2006 |

(Continued)

OTHER PUBLICATIONS

United States Patent and Trademark Office; Office Action; Office Action from U.S. Appl. No. 15/205,357; pp. 1-16; publisher United States Patent and Trademark Office; published Alexandria, Virginia, USA; copyright and dated Dec. 23, 2016; (16 pages).

(Continued)

*Primary Examiner* — Rene Towa
(74) *Attorney, Agent, or Firm* — Metz Lewis Brodman Must O'Keefe LLC

(57) ABSTRACT

A device for penetrating tissue is provided that has a driving actuator with a body and motor shaft that is reciprocated. A coupler is attached to the motor shaft, and a key engages the driving actuator and coupler and limits rotational motion of the motor shaft and permits linear motion of the motor shaft. A penetrating member is carried by the coupler, and linear motion of the motor shaft is translated to the penetrating member to linearly reciprocate the penetrating member.

35 Claims, 21 Drawing Sheets

Related U.S. Application Data application No. 13/672,482, filed on Nov. 8, 2012, now Pat. No. 8,777,871, which is a continuation of application No. 12/559,383, filed on Sep. 14, 2009, now Pat. No. 8,328,738, which is a continuation-in-part of application No. 12/163,071, filed on Jun. 27, 2008, now Pat. No. 8,043,229.

(60) Provisional application No. 61/895,789, filed on Oct. 25, 2013, provisional application No. 61/089,756, filed on Sep. 15, 2008, provisional application No. 60/937,749, filed on Jun. 29, 2007.

(51) Int. Cl.

| | |
|---|---|
| *A61M 25/00* | (2006.01) |
| *A61B 10/02* | (2006.01) |
| *A61M 5/32* | (2006.01) |
| *A61B 17/32* | (2006.01) |
| *A61B 17/00* | (2006.01) |
| *A61B 90/00* | (2016.01) |

(52) U.S. Cl.
CPC ...... *A61B 17/3415* (2013.01); *A61B 17/3496* (2013.01); *A61M 5/3287* (2013.01); *A61M 25/0084* (2013.01); *A61B 17/320068* (2013.01); *A61B 2017/00115* (2013.01); *A61B 2017/00123* (2013.01); *A61B 2090/064* (2016.02)

(58) Field of Classification Search
CPC .............. A61B 17/3415; A61B 10/025; A61B 17/3401; A61B 17/3496; A61B 2090/064; A61B 2017/00123; A61M 5/3287; A61M 25/0084
See application file for complete search history.

(56) References Cited

U.S. PATENT DOCUMENTS

| | | | |
|---|---|---|---|
| 4,623,335 A | 11/1986 | Jackson | |
| 4,648,406 A | 3/1987 | Miller | |
| 4,771,660 A | 9/1988 | Yacowitz | |
| 4,801,293 A | 1/1989 | Jackson | |
| 4,911,161 A * | 3/1990 | Schechter | A61F 9/0133 |
| | | | 606/107 |
| 5,024,662 A | 6/1991 | Menes et al. | |
| 5,151,083 A * | 9/1992 | Pichler | A61B 17/320068 |
| | | | 604/19 |
| 5,217,478 A * | 6/1993 | Rexroth | A61B 17/32002 |
| | | | 606/172 |
| 5,221,282 A * | 6/1993 | Wuchinich | A61B 17/320068 |
| | | | 606/99 |
| 5,320,613 A | 6/1994 | Houge | |
| 5,403,276 A * | 4/1995 | Schechter | A61B 17/32002 |
| | | | 604/118 |
| 5,449,370 A | 9/1995 | Vaitekunas | |
| 5,471,102 A | 11/1995 | Becker et al. | |
| 5,526,820 A | 6/1996 | Khoury | |
| 5,575,789 A * | 11/1996 | Bell | A61B 18/00 |
| | | | 606/10 |
| 5,647,851 A * | 7/1997 | Pokras | A61M 5/20 |
| | | | 604/131 |
| 5,681,283 A | 10/1997 | Brownfield | |
| 5,711,302 A | 1/1998 | Larnpropoulos | |
| 5,728,089 A | 3/1998 | Lal et al. | |
| 5,728,130 A | 3/1998 | Ishikawa et al. | |
| 5,729,077 A | 3/1998 | Newnham et al. | |
| 5,735,813 A | 4/1998 | Lewis | |
| 5,769,086 A | 6/1998 | Ritchart | |
| 5,840,026 A | 11/1998 | Uber, III et al. | |
| 5,843,109 A * | 12/1998 | Mehta | B06B 1/0618 |
| | | | 604/22 |
| 5,865,764 A | 2/1999 | Moorhead | |
| 5,871,470 A | 2/1999 | McWha | |
| 5,885,226 A | 3/1999 | Rubinstein et al. | |
| 5,954,701 A | 9/1999 | Matalon | |
| 6,019,775 A | 2/2000 | Sakurai | |
| 6,019,776 A | 2/2000 | Preissman et al. | |
| 6,068,604 A * | 5/2000 | Krause | G01N 3/405 |
| | | | 600/587 |
| 6,096,004 A | 8/2000 | Meglan et al. | |
| 6,190,333 B1 | 2/2001 | Valencia | |
| 6,245,028 B1 | 6/2001 | Furst et al. | |
| 6,273,861 B1 | 8/2001 | Bates et al. | |
| 6,379,371 B1 | 4/2002 | Novak et al. | |
| 6,402,701 B1 * | 6/2002 | Kaplan | A61B 10/0233 |
| | | | 600/567 |
| 6,423,014 B1 | 7/2002 | Churchill et al. | |
| 6,443,910 B1 | 9/2002 | Krueger et al. | |
| 6,465,936 B1 | 10/2002 | Knowles et al. | |
| 6,402,769 B1 | 11/2002 | Boukhny | |
| 6,491,708 B2 | 12/2002 | Madan et al. | |
| 6,497,714 B1 | 12/2002 | Ishikawa et al. | |
| 6,514,267 B2 | 2/2003 | Jewett | |
| 6,602,229 B2 | 8/2003 | Coss | |
| 6,623,429 B2 | 9/2003 | Percival | |
| 6,629,922 B1 | 10/2003 | Puria | |
| 6,664,712 B2 | 12/2003 | Rayner | |
| 6,673,086 B1 | 1/2004 | Hofmeier et al. | |
| 6,689,087 B2 | 2/2004 | Pal et al. | |
| 6,702,761 B1 * | 3/2004 | Damadian | A61B 10/0233 |
| | | | 600/567 |
| 6,718,196 B1 | 4/2004 | Mah et al. | |
| 6,726,698 B2 | 4/2004 | Cimino | |
| 6,730,043 B2 | 5/2004 | Krueger et al. | |
| 6,785,572 B2 | 8/2004 | Yanof et al. | |
| 6,817,973 B2 | 11/2004 | Merril et al. | |
| 6,869,439 B2 | 3/2005 | White et al. | |
| 6,939,317 B2 | 9/2005 | Zacharias | |
| 6,942,677 B2 | 9/2005 | Nita et al. | |
| 6,984,220 B2 | 1/2006 | Wuchinich | |
| 7,018,343 B2 | 3/2006 | Plishka | |
| 7,025,774 B2 | 4/2006 | Freeman et al. | |
| 7,206,626 B2 | 4/2007 | Quaid, III | |
| 7,297,131 B2 | 11/2007 | Nita | |
| 7,335,997 B2 | 2/2008 | Wiener | |
| 7,364,567 B2 | 4/2008 | Beyerlein | |
| 7,374,544 B2 | 5/2008 | Freeman et al. | |
| 7,518,479 B2 | 4/2009 | Mask et al. | |
| 7,585,280 B2 | 9/2009 | Wilson | |
| 7,618,409 B2 | 11/2009 | Hochman | |
| 7,648,468 B2 | 1/2010 | Boecker et al. | |
| 7,651,475 B2 | 1/2010 | Angel et al. | |
| 7,651,490 B2 | 1/2010 | Boukhny et al. | |
| 7,654,825 B2 | 2/2010 | Ray | |
| 7,776,027 B2 | 8/2010 | Manna et al. | |
| 7,896,833 B2 | 3/2011 | Hochman | |
| 7,922,689 B2 | 4/2011 | Lechner | |
| 7,955,301 B1 | 6/2011 | McKay | |
| 8,043,308 B2 | 10/2011 | Bittenson | |
| 8,075,496 B2 | 12/2011 | Deck | |
| 8,142,365 B2 | 3/2012 | Miller | |
| 8,231,645 B2 | 7/2012 | List | |
| 2001/0014785 A1 | 8/2001 | Sussman et al. | |
| 2002/0010390 A1 | 1/2002 | Guice | |
| 2002/0026127 A1 | 2/2002 | Balbierz et al. | |
| 2002/0042594 A1 | 4/2002 | Lum | |
| 2002/0049462 A1* | 4/2002 | Friedman | A61B 17/320068 |
| | | | 606/169 |
| 2002/0077589 A1 | 6/2002 | Tessari | |
| 2002/0109433 A1 | 8/2002 | Rayner | |
| 2002/0183774 A1 | 12/2002 | Witt et al. | |
| 2002/0198555 A1 | 12/2002 | White et al. | |
| 2003/0040737 A1 | 2/2003 | Merril | |
| 2003/0078495 A1 | 4/2003 | Goodwin | |
| 2003/0109871 A1 | 6/2003 | Johnson et al. | |
| 2003/0195468 A1 | 10/2003 | Lal et al. | |
| 2003/0199899 A1 | 10/2003 | Boecker et al. | |
| 2003/0199909 A1 | 10/2003 | Boecker | |
| 2004/0010204 A1 | 1/2004 | Weber | |
| 2004/0010251 A1 | 1/2004 | Pitaru | |

(56) References Cited

U.S. PATENT DOCUMENTS

| | | |
|---|---|---|
| 2004/0024358 A1 | 2/2004 | Meythaler |
| 2004/0049216 A1* | 3/2004 | Verdaasdonk ............................... A61B 17/320068 606/169 |
| 2004/0082884 A1* | 4/2004 | Pal .................... A61B 17/16 601/2 |
| 2004/0106894 A1 | 6/2004 | Hunter et al. |
| 2004/0215080 A1 | 10/2004 | Lechner |
| 2004/0260240 A1 | 12/2004 | Beyerlein |
| 2005/0070458 A1 | 3/2005 | John |
| 2005/0131345 A1 | 6/2005 | Miller |
| 2005/0148940 A1 | 7/2005 | Miller |
| 2005/0177201 A1 | 8/2005 | Freeman |
| 2006/0058783 A1 | 3/2006 | Buchman, III |
| 2006/0122555 A1 | 6/2006 | Hochman |
| 2006/0129091 A1 | 6/2006 | Bonnette |
| 2006/0135882 A1 | 6/2006 | Bleich |
| 2006/0142657 A1 | 6/2006 | Quaid et al. |
| 2006/0149141 A1 | 7/2006 | Sheets |
| 2006/0149161 A1 | 7/2006 | Wilson |
| 2006/0195043 A1 | 8/2006 | Rutherford |
| 2006/0224144 A1* | 10/2006 | Lee ..................... A61M 1/0009 604/542 |
| 2007/0038129 A1 | 2/2007 | Kishimoto |
| 2007/0063618 A1* | 3/2007 | Bromfield ...... A61B 17/320068 310/323.19 |
| 2007/0079455 A1 | 4/2007 | Brewer |
| 2007/0088297 A1 | 4/2007 | Redding |
| 2007/0088376 A1* | 4/2007 | Zacharias ......... A61B 17/32002 606/169 |
| 2007/0106158 A1* | 5/2007 | Madan .................. A61B 8/4455 600/459 |
| 2007/0123888 A1 | 5/2007 | Bleich |
| 2007/0129628 A1 | 6/2007 | Hirsh |
| 2007/0129732 A1* | 6/2007 | Zacharias ...... A61B 17/320068 606/107 |
| 2007/0142766 A1 | 6/2007 | Sundar et al. |
| 2007/0191758 A1 | 8/2007 | Hunter et al. |
| 2007/0219496 A1 | 9/2007 | Kamen et al. |
| 2007/0250113 A1 | 10/2007 | Hegeman et al. |
| 2007/0255220 A1 | 11/2007 | King |
| 2008/0021490 A1 | 1/2008 | Briggs et al. |
| 2008/0055028 A1* | 3/2008 | Mask ................ A61M 37/0084 335/229 |
| 2008/0097287 A1 | 4/2008 | Nelson |
| 2008/0103413 A1 | 5/2008 | Cicenas et al. |
| 2008/0139961 A1 | 6/2008 | Slama et al. |
| 2008/0147094 A1* | 6/2008 | Bittenson ........... A61B 17/0482 606/144 |
| 2008/0154188 A1 | 6/2008 | Hochman |
| 2008/0228104 A1 | 9/2008 | Uber et al. |
| 2008/0255444 A1 | 10/2008 | Li |
| 2009/0005703 A1 | 1/2009 | Fasciano |
| 2009/0069712 A1 | 3/2009 | Mulvihill et al. |
| 2009/0131830 A1 | 5/2009 | Freeman |
| 2009/0131832 A1 | 5/2009 | Sacristan Rock |
| 2009/0157044 A1 | 6/2009 | Liyanagama |
| 2009/0204119 A1 | 8/2009 | Bleich |
| 2009/0240205 A1 | 9/2009 | Wen |
| 2009/0247865 A1 | 10/2009 | Spohn et al. |
| 2009/0270759 A1 | 10/2009 | Wilson |
| 2010/0004558 A1 | 1/2010 | Frankhouser |
| 2010/0010505 A1 | 1/2010 | Herlihy et al. |
| 2010/0036245 A1 | 2/2010 | Yu et al. |
| 2010/0036256 A1 | 2/2010 | Boukhny |
| 2010/0069828 A1 | 3/2010 | Steen |
| 2010/0069851 A1 | 3/2010 | Vad |
| 2010/0094143 A1 | 4/2010 | Mahapatra |
| 2011/0004159 A1 | 1/2011 | Nelson |
| 2011/0125107 A1 | 5/2011 | Slocum |
| 2011/0130758 A9 | 6/2011 | Bleich |
| 2011/0224623 A1 | 9/2011 | Velez Rivera |
| 2011/0298628 A1 | 12/2011 | Vad |
| 2012/0078231 A1 | 3/2012 | Hoshinouchi |
| 2012/0210569 A1 | 8/2012 | Schmitt |
| 2012/0220942 A1 | 8/2012 | Hall |
| 2012/0232488 A1* | 9/2012 | Aviles ................... A61M 25/02 604/177 |
| 2013/0072856 A1 | 3/2013 | Frankhouser et al. |
| 2014/0142553 A1* | 5/2014 | Poncon ................. A61M 5/345 604/533 |
| 2014/0299568 A1* | 10/2014 | Browne ................ A61J 1/2096 215/247 |
| 2015/0182232 A1 | 7/2015 | Peterson |
| 2015/0283334 A1 | 10/2015 | Marx et al. |
| 2015/0297404 A1* | 10/2015 | Kang .................. A61F 9/00736 606/166 |
| 2015/0297449 A1* | 10/2015 | Browne ............... B65D 51/002 604/404 |
| 2015/0306358 A1 | 10/2015 | Duffy |

FOREIGN PATENT DOCUMENTS

| | | |
|---|---|---|
| JP | 9239031 | 9/1997 |
| JP | 2001346874 | 12/2001 |
| WO | 2004091693 | 10/2004 |
| WO | 2008086560 | 7/2008 |
| WO | 2008097609 | 8/2008 |
| WO | 2009083600 | 7/2009 |
| WO | 2009092164 | 7/2009 |
| WO | 2009097621 | 8/2009 |

OTHER PUBLICATIONS

International Searching Authority; International Search Report and Written Opinion of the International Searching Authority; International Application No. PCT/US2014/062099; Patent Cooperation Treaty; pp. 1-10; publisher United States Intearnatinal Searching Authority; Published Alexandria, Virginia, US; copyright and dated Mar. 11, 2015; (10 pages).

Meyer Jr., R.J., et al., "Displacement Amplification of Electroactive Materials Using the Cymbal Flextensional Transducer", Sensors and Actuators A 87 (2001) 157-162.

Podder, T.K., et al., "Effects of Velocity Modulation During Surgical Needle Insertion", Proceedings of the 2005 IEEE, Engineering in Medicine and Biology 27th Annual Conference, Sep. 1-4, 2005.

Luis, J., et al., "Rectangular Cymbal Arrays for Improved Ultrasonic Transdermal Insulin Delivery", J. Acoust. Soc. Am., vol. 122, Issue 4, Oct. 2007.

Yang, M., et al., "Microneedle Insertion Force Reduction Using Vibratory Actuation", Biomedical Microdevices 6:3, 177-182, 2004.

Zorcolo, et al., "Catheter Insertion Simulation With Combined Visual and Haptic Feedback", Center for Advanced Studies, Research and Development in Sardinia 09101 Uta (CA) Italy.

Piccin, et al., "A Robotized Needle Insertion Device for Percutaneous Procedures", Proceedings of IDETC/CIE 2005, 2006 ASME International Design Engineering Technical Conferences and Computers and Information in Engineering Conference, Long Beach, CA, USA, Sep. 24-28, 2005.

Loeffel, et al., "Development of an Advanced Injection Device for Highly Viscous Materials", European Cells and Materials, vol. 11, Supp. 1, 2006, p. 51.

Dario, et al., "Small Surgical Tools and Augmenting Devices", IEEE Transactions on Robotics and Automation, vol. 19, No. 5, Oct. 2003, pp. 782-792.

"Sonic Drill Could Go Into Space", R&D, Sep. 2000, p. 135.

Goethals, P., "Tactile Feedback for Robot Assisted Minimally Invasive Surgery: An Overview", Division PMA, Department of Engineering, K.U. Leuven, Jul. 14, 2008.

Zorcolo, et al., "Catheter Insertion Simulation with Combined Visual and Haptic Feedback", Center for Advanced Studies, Research and Development in Sardinia, 09101 Uta (CA) Italy; Proceedings of the First PHANToM Users Research Symposium, May 21-22, 1999, Deutsches Krebsfordschungszentrum, Heidelberg, Germany.

"Mark V ProVis Angiographic Injection System", Medrad, Inc., Copyright 2006-2010.

(56) References Cited

OTHER PUBLICATIONS

Kwon, et al., "Realistic Force Reflection in the Spine Biopsy Simulator", IEEE International Conference on Robotics and Automation, 2001. Proceedings 2001 ICRA, May 21-26, 2001, Seoul, Korea 2001, vol. 2, 1358-1363.

"R&D 100 Awards Winners Reveal 21st Century Technologies", 38th Annual R&D Awards, R&D Research & Development, Sep. 2000, p. 135.

"Silicon-Based Ultrasonic Surgical Actuators", Amit Lal, Member, IEEE; Proceedings of the 20th Annual International Conference of the IEEE Engineering in Medicine and Biology Society, vol. 20, No. 6, 1998, pp. 2785-2790.

Terrett, et al., "3538 Study Assessing the Effectiveness of a Vibrating Dental Syringe Attachment", Pain Management, Oral Pathology, Malodor, and Indices, Mar. 13, 2004.

Lal, "Silicon-Based Ultrasonic Surgical Actuators", Proceedings of the 20th Annual Conference of the IEEE in Medicine and Biology Society, vol. 20, No. 6, 1998, pp. 2785-2790.

Hing, et al., Reality-Based Needle Insertion Simulation for Haptic Feedback in Prostate Brachytherapy, Proceedings of the 2006 IEEE International Conference on Robotics and Automation, Orlando, Florida, May 2006.

Hing, et al., "Reality-Based Estimation of Needle and Soft-Tissue Interaction for Accurate Haptic Feedback in Prostate Brachytherapy Simulation", Program for Robotics, Intelligent Sensing, and Mechatronics (PRISM) Laboratory, Drexel University, Philadelphia, PA, Drexel University College of Medicine, Philadelphia, PA.

International Preliminary Report on Patentability for PCT Application No. PCT/AU2008/000019, dated Jul. 21, 2009.

International Search Report for PCT Application No. PCT/US2009/060387, dated May 18, 2010.

International Search Report for PCT Application No. PCT/US2009/056864, dated Apr. 26, 2010.

United States Patent and Trademark Office; Office Action; Office Action from U.S. Appl. No. 13/222,363;copyright and dated Dec. 11, 2014; pp. 1-9; publisher United States Patent and Trademark Office; Published Alexandria, Virginia, USA; copyright and dated Dec. 11, 2014; (9 pages).

United States Patent and Trademark Office; Office Action; Office Action from U.S. Appl. No. 14/329,177; copyright and dated Nov. 18, 2014; pp. 1-19; publisher United States Patent and Trademark Office; Published Alexandria, Virginia, USA; copyright and dated Nov. 18, 2014; (19 pages).

United States Patent and Trademark Office; Office Action; Office Action from U.S. Appl. No. 15/205,357; pp. 1-48; publisher United States Patent and Trademark Office; published Alexandria, Virginia, USA; copyright and dated Jun. 22, 2017; (48 pages).

* cited by examiner

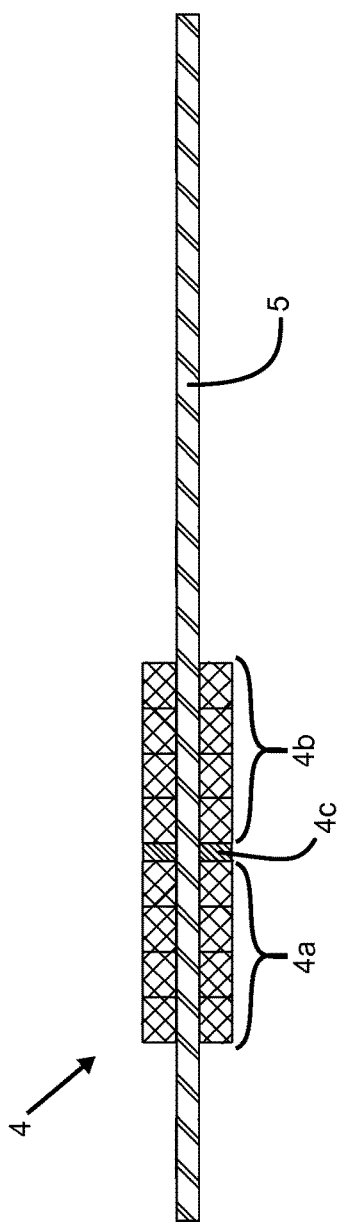
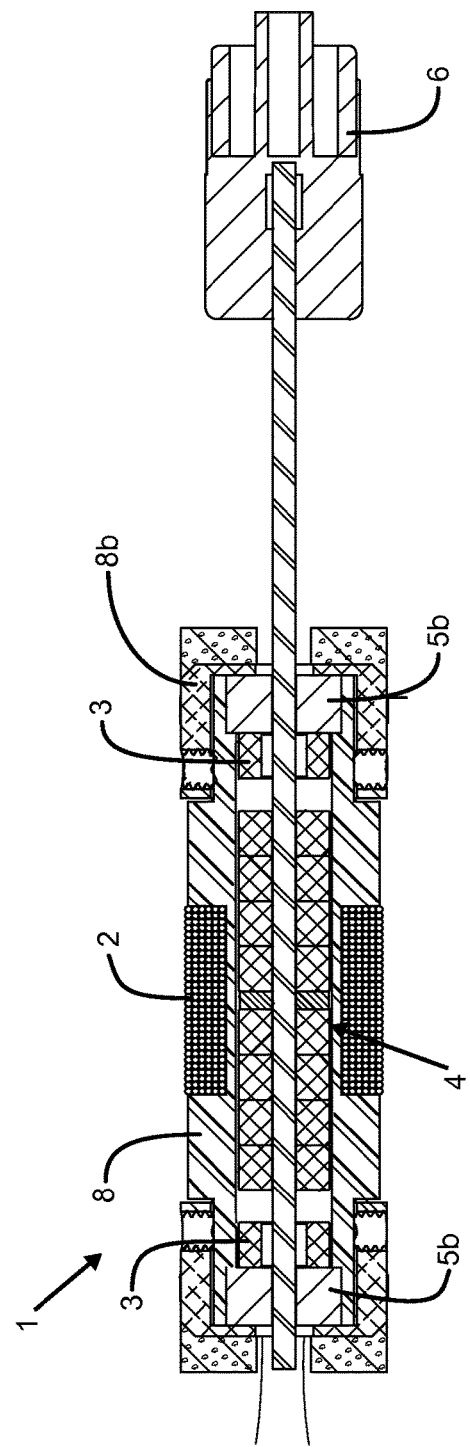
FIG. 1B
FIG. 1C

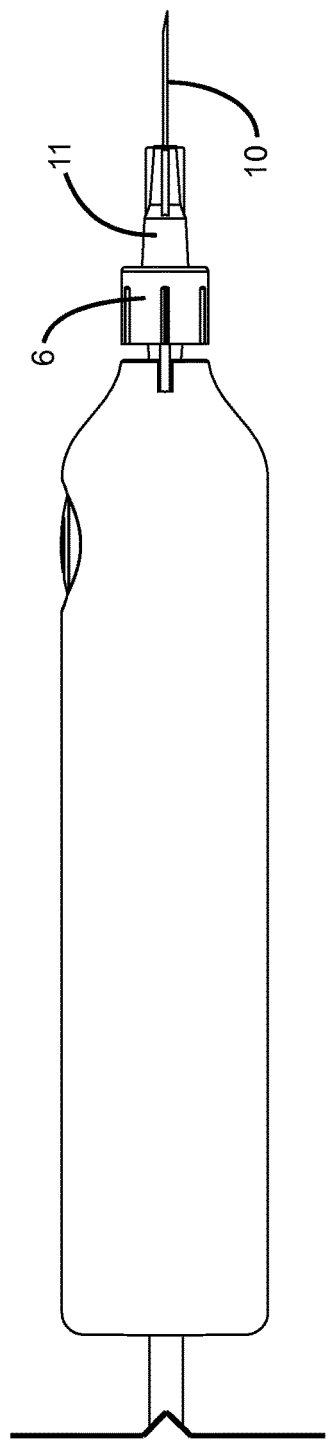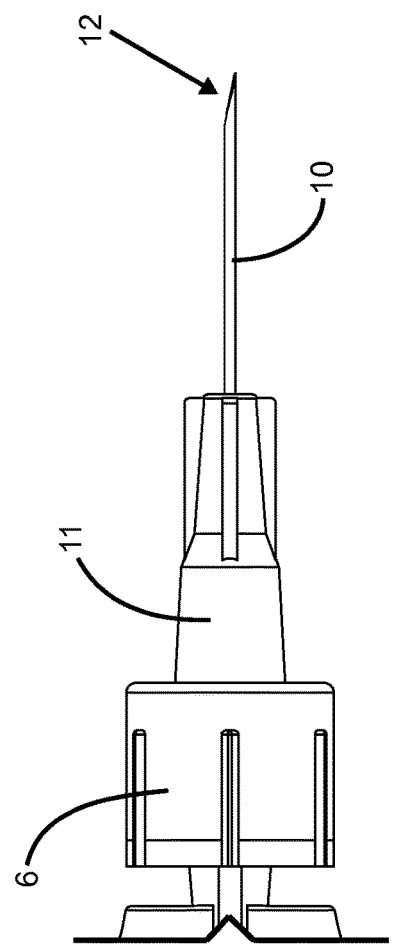
FIG. 2A
FIG. 2B

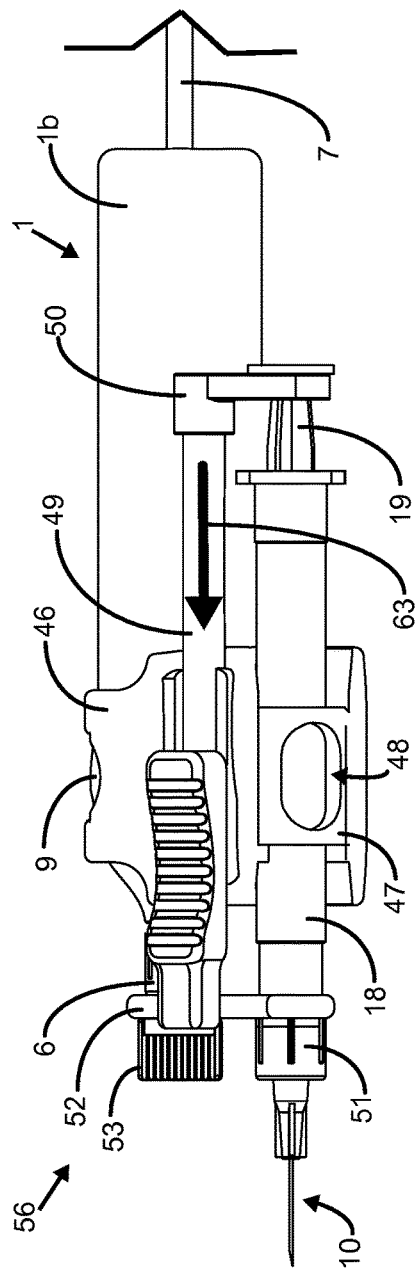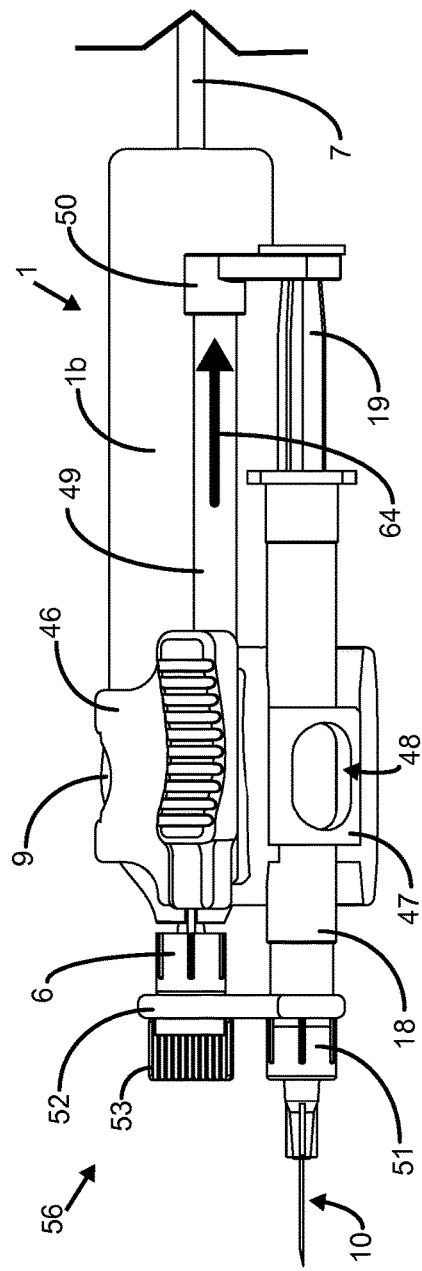

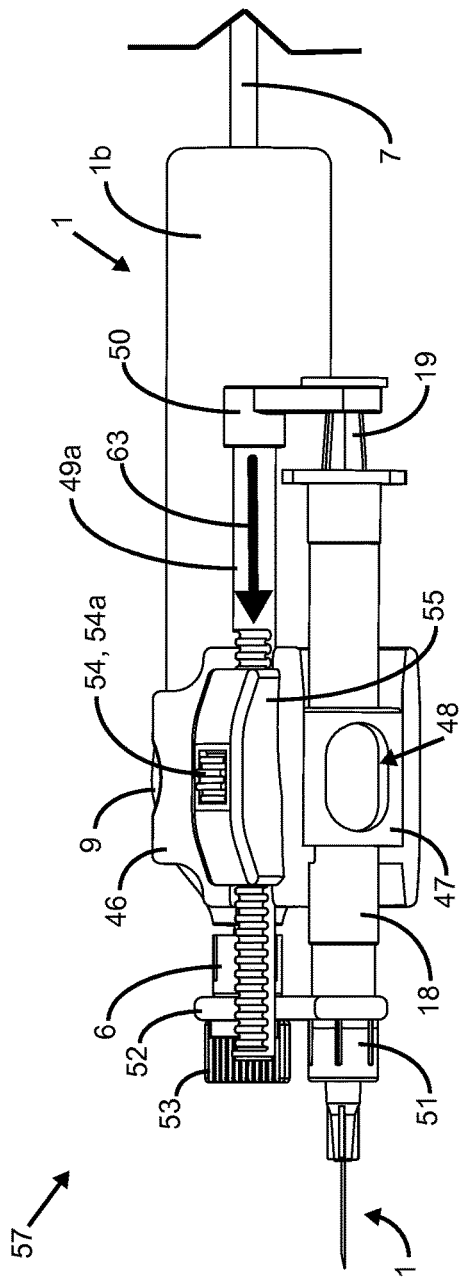
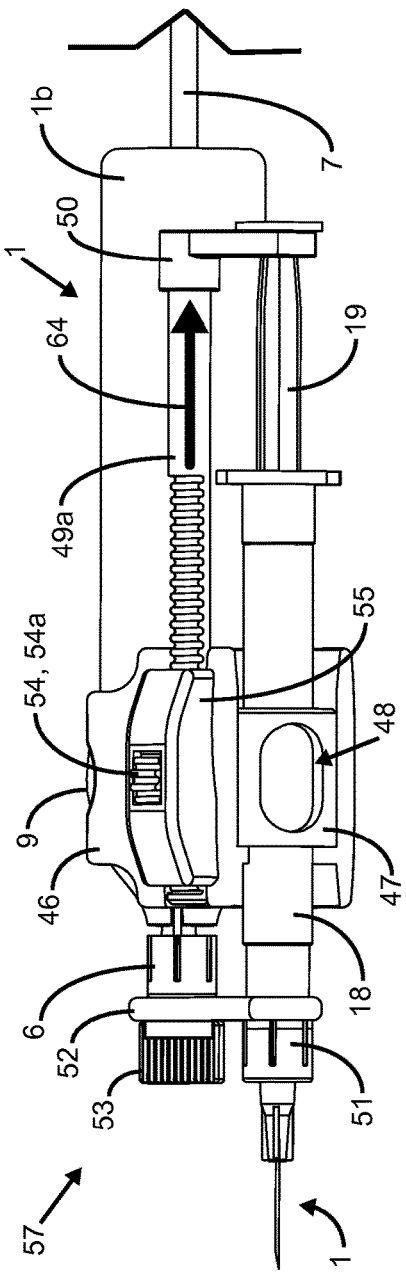
FIG. 8A
FIG. 8B

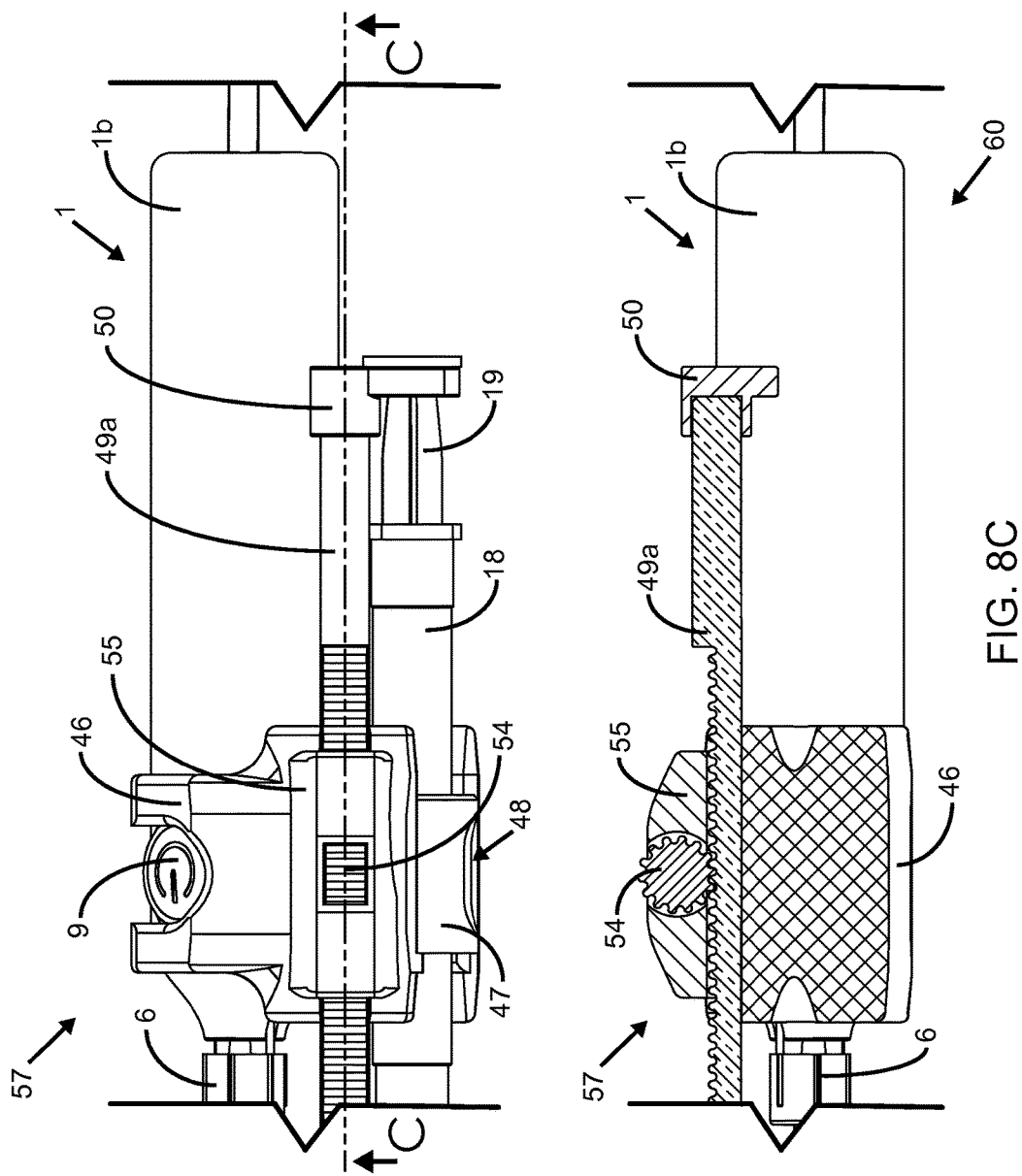

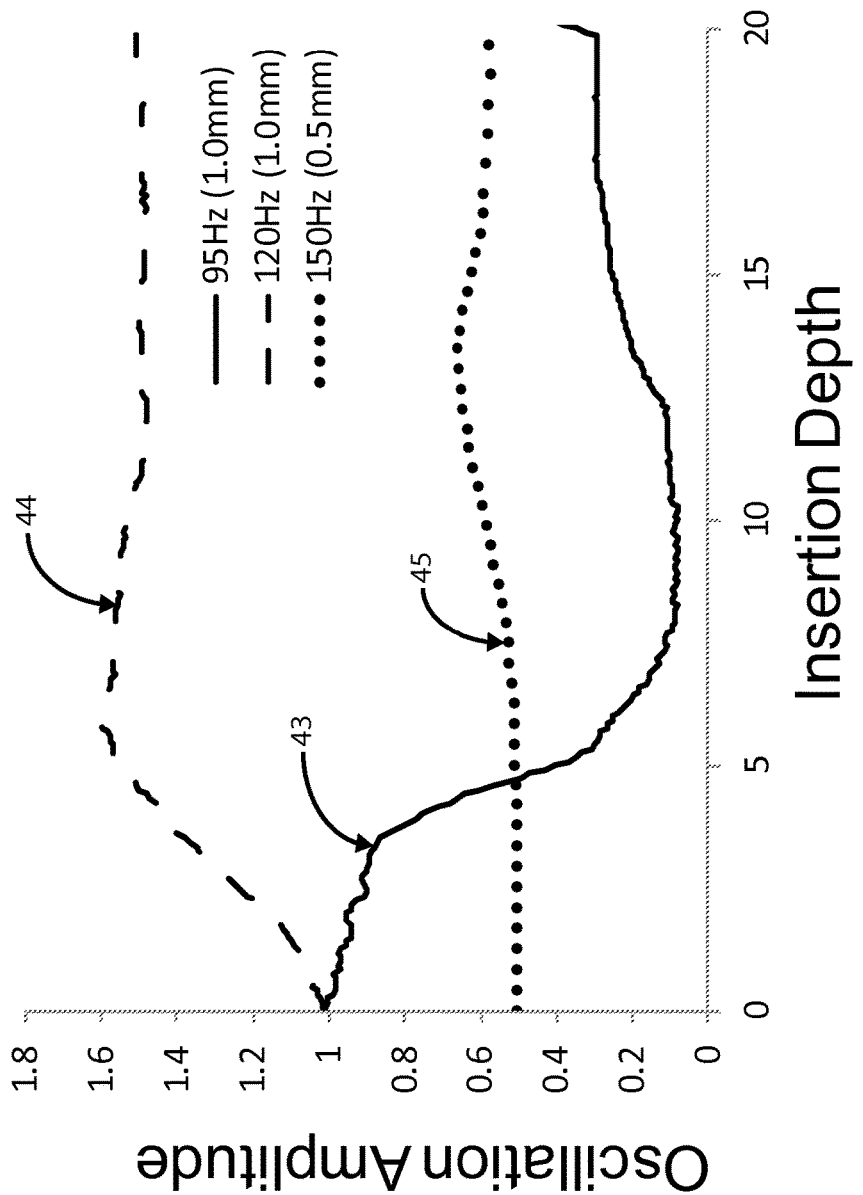

DEVICE AND METHOD FOR LESS FORCEFUL TISSUE PUNCTURE

CROSS REFERENCE TO RELATED APPLICATION

This application claims the benefit under 35 U.S.C § 119(e) of U.S. Provisional Application Ser. No. 61/895,789 filed on Oct. 25, 2013 and entitled, "DEVICE AND METHOD FOR LESS FORCEFUL TISSUE PUNCTURE." U.S. Provisional Application Ser. No. 61/895,789 is incorporated by reference herein in its entirety for all purposes. This application is also a continuation-in-part application and claims the benefit under 35 U.S.C. § 120 of U.S. application Ser. No. 14/329,177, filed on Jul. 11, 2014, entitled Medical Tool for Reduced Penetration Force with Feedback Means. U.S. application Ser. No. 14/329,117 is incorporated by reference herein in its entirety for all purposes. U.S. application Ser. No. 14/329,117 is a continuation application and claims the benefit under 35 U.S.C. § 120 of U.S. application Ser. No. 13/672,482, filed on Nov. 8, 2012, entitled MEDICAL TOOL FOR REDUCED PENETRATION FORCE WITH FEEDBACK MEANS, which issued as U.S. Pat. No. 8,777,871 on Jul. 15, 2014. U.S. application Ser. No. 13/672,482 is a continuation application that claims the benefit under 35 U.S.C. § 120 of U.S. application Ser. No. 12/559,383, filed on Sep. 14, 2009, entitled MEDICAL TOOL FOR REDUCED PENETRATION FORCE WITH FEEDBACK MEANS, which issued as U.S. Pat. No. 8,328,738 on Dec. 11, 2012 which claims the benefit under 35 U.S.C. § 119(e) of U.S. Provisional Application Ser. No. 61/089,756 filed on Sep. 15, 2008 entitled MEDICAL TOOL FOR REDUCED PENETRATION FORCE WITH FEEDBACK MEANS, and also is a continuation-in-part application and claims the benefit under 35 U.S.C. § 120 of U.S. application Ser. No. 12/163,071 filed on Jun. 27, 2008 entitled MEDICAL TOOL FOR REDUCED PENETRATION FORCE, which issued as U.S. Pat. No. 8,043,229 on Oct. 25, 2011, which in turn claims the benefit under 35 U.S.C. § 119(e) of U.S. Provisional Application Ser. No. 60/937,749 filed on Jun. 29, 2007 entitled RESONANCE DRIVEN VASCULAR ENTRY NEEDLE and all of whose entire disclosures are incorporated by reference herein in their entireties for all purposes.

STATEMENT REGARDING FEDERALLY SPONSORED RESEARCH OR DEVELOPMENT

This invention was made with government support under RR024943 and AG037214 awarded by the National Institutes of Health, and 2013-33610-20821 awarded by the USDA. The government has certain rights in the invention.

FIELD OF THE INVENTION

The present invention generally pertains to handheld medical, veterinary, and pre-clinical or laboratory research devices, and more specifically to electrically driven lancets, needles, epidural catheter inserters, biopsy instruments, vascular entry instruments, spinal access needles, and other catheterization needles. The invention is applicable to the delivery and removal of blood, tissues, medicine, nutrients, or other materials within the body.

BACKGROUND

In the fields of medicine, veterinary, and pre-clinical or laboratory research the need to insert penetrating members (such as needles and lancets) into living tissues is ubiquitous. Some of the reasons necessitating tissue penetration and insertion of penetrating members include: to inject medications and vaccines, to obtain samples of bodily fluids such as blood, to acquire a tissue sample such as for biopsy, or to provide short or long term access to the vascular system such as intravenous (IV) catheter placement.

Of the 39 million patients hospitalized in the United States, 31 million (80%) receive an IV catheter for nutrition, medication, and fluids. Obtaining peripheral venous access is complicated by loose tissue, scar tissue from repeat sticks, hypotension, hypovolemic shock, and/or dehydration. These factors manifest in easily collapsed veins, rolling veins, scarred veins, and fragile veins making venipuncture problematic. Most hospitals allow a clinician to make several attempts at peripheral IV access before the hospital "IV team" is called. Studies have shown that success can improve significantly with experience. There are also a number of techniques that can be used such as tourniquets, nitroglycerin ointment, hand/arm warming, but these require additional time, are cumbersome, and do not work effectively in all situations. Tools are also available to improve visualization of the vasculature that use illumination, infrared imaging, or ultrasound. These tools, however, do not simplify peripheral venous access into a collapsible vein. In emergency situations, a clinician will often insert a central venous catheter (CVC) or possibly an intraosseous line. These procedures are more invasive, costly, and higher risk. Multiple needle sticks significantly increase patient anxiety and pain, leading to decreased patient cooperation, vasoconstriction, and greater opportunity for infection and complications. Repeated attempts to obtain venous access are costly to the healthcare facility; estimated at over $200,000 annually for a small hospital. In endoscopy facilities, which see large numbers of older patients, the problem is further exacerbated by fasting requirements that decreases the pressure in the veins. During cannulation, the needle and catheter push the near wall of the vein into the far wall, collapsing the vein—inhibiting the ability to place the needle into the inner lumen of the vein.

Tissue deformation during needle insertion is also an issue for soft tissue biopsy of tumors or lesions. Conventional needles tend to deform the tissue during the insertion, which can cause misalignment of the needle path and the target area to be sampled. The amount of tissue deformation can be partially reduced by increasing the needle insertion velocity, and so this property has been exploited by biopsy guns on the market today.

Blood sampling is one of the more common procedures in biomedical research involving laboratory animals, such as mice and rats. A number of techniques and routes for obtaining blood samples exist. Some routes require/recommend anesthesia (such as jugular or retro-orbital), while others do not (such as tail vein/artery, saphenous vein or submandibular vein). All techniques utilize a sharp (lancet, hypodermic needle, or pointed scalpel) that is manually forced into the tissue to produce a puncture that bleeds. A capillary tube is positioned over the puncture site to collect the blood droplets for analysis, or the blood may be collected into a syringe or vacuum vial. Regardless of the sharp used, if an individual is properly trained the procedure can be performed quickly to minimize pain and stress. It is important to minimize stress as this can interfere with blood chemistry analysis, particularly for stress-related hormones. Another much more expensive strategy is to place an indwelling catheter and obtain blood samples in an automated device. However, the catheter cannot be left in over the life span. In addition, the tethering jackets and cables, which must remain in contact with the animal, will likely cause stress. Microneedles can be implanted with highly reduced insertion force and less pain, but may not produce a large enough puncture to yield significant blood for collection and analysis.

Research supports that needle vibration, or oscillation, causes a reduction in needle insertion forces. The increased needle velocity from oscillation results in decreased tissue deformation, energy absorbed, penetration force, and tissue damage. These effects are partly due to the viscoelastic properties of the biological tissue and can be understood through a modified non-linear Kelvin model that captures the force-deformation response of soft tissue. Since internal tissue deformation for viscoelastic bodies is dependent on velocity, increasing the needle insertion speed results in less tissue deformation. The reduced tissue deformation prior to crack extension increases the rate at which energy is released from the crack, and ultimately reduces the force of rupture. The reduction in force and tissue deformation from the increased rate of needle insertion is especially significant in tissues with high water content such as soft tissue. In addition to reducing the forces associated with cutting into tissue, research has also shown that needle oscillation during insertion reduces the frictional forces between the needle and surrounding tissues.

Recently, a number of vibration devices have been marketed that make use of the Gate's Control Theory of Pain. The basic idea is that the neural processing, and therefore perception of pain, can be minimized or eliminated by competing tactile sensations near the area of pain (or potential pain) originates. Vibrational devices may be placed on the skin in attempt to provide "vibrational anesthesia" to an area prior to, or possibly during, a needle insertion event. Research has shown that tissue penetration with lower insertion forces results in reduced pain. The Gate Control Theory of Pain provides theoretical support for the anesthetic effect of vibration. The needle vibration may stimulate non-nociceptive Aβ fibers and inhibit perception of pain and alleviate the sensation of pain at the spinal cord level. In nature, a mosquito vibrates it's proboscis at a frequency of 17-400 Hz to reduce pain and improve tissue penetration.

Other vibrating devices directly attach to a needle-carrying syringe and employ non-directional vibration of the needle during insertion. Reports suggest that this type of approach can ease the pain of needle insertion for administering local anesthetic during dental procedures, and to enhance the treatment of patients undergoing sclerotherapy. These non-directed vibration techniques do not allow for precise direct control of the needle tip displacements, and by their nature induce vibrations out of the plane of insertion, which could increase the risk for tissue damage during insertion. Furthermore, existing vibrational devices for improving needle insertion cannot be readily integrated into a control system which would allow for the ability to control and/or maintain the magnitude of needle oscillation during insertion through a wide range of tissue types.

A need exists to improve the insertion of penetrating members (such as needles or lancets), by reducing the force required to insert them, causing less tissue deformation, and inducing less pain and stress to the patient, research subject, and clinician/researcher. As such, there remains room for variation and improvement within the art.

SUMMARY

Various features and advantages of the invention will be set forth in part in the following description, or may be obvious from the description, or may be learned from practice of the invention.

The invention provides in one exemplary embodiment a handheld device that provides axially-directed oscillatory motion (also referred to as reciprocating motion) to a detachable penetrating member (such as but not limited to lancets, needles, epidural catheters, biopsy instruments, and vascular entry instruments) at a distal end, for use in procedures (such as but not limited to vascular entry, catheterization, and blood collection). The device comprises at least one linear reciprocating actuator that can be reversibly attached to a penetrating member or other composite system which itself contains a penetrating member, and wherein the driving actuator provides motion to the penetrating member, causing it to reciprocate at small displacements, thereby reducing the force required to penetrate through tissues. Reciprocating motion of the penetrating member facilitates less tissue displacement and drag, enabling, for example, easier access into rolling or collapsed vasculature. Specific applications of the invention include, but are not limited to, penetration of tissues for delivery or removal of bodily fluids, tissues, nutrients, medicines, therapies, and placement or removal of catheters. This device is for inserting penetrating members into the body, including human or animal subjects, for a variety of applications.

The handheld device disclosed may be a driving actuator composed of a handpiece body housing at least one oscillatory linear actuator. The actuator is preferably a voice coil motor (VCM) but may alternatively be implemented with a DC motor, solenoid, piezoelectric actuator, or linear vibration motor disposed within the handpiece body. The linear actuator causes a motor shaft to oscillate or vibrate back and forth relative to the handpiece body, in the axial direction of the shaft. Attached to one end of the shaft is a coupling mechanism which enables reversible attachment of a penetrating member (or to a separate device that already has a penetrating member attached to it).

The need for reversible attachment to a range of penetrating members or separate devices that employ a penetrating member, requires a number of different attachment schemes in order to cause linear, reciprocating motion of the penetrating member. In the preferred embodiment the handheld device has a coupler that enables reversible attachment of LUER-Slip® (slip tip) or LUER-Lok® (LUER-Lock) style needle or lancet hubs. In another embodiment of the device, a custom connection enables reversible attachment of separate devices with a penetrating member (such as syringe with attached needle or a safety IV-access device) which allows the linear actuator to vibrate the composite system, thereby resulting in reciprocating motion being delivered to the attached penetrating member.

Additional features include embodiments that enable delivery or removal of fluids down the lumen of hollow penetrating members, via side port that allows access to the inner lumen. Tubing that is sufficiently compliant so as not to impede the reciprocating motion of the actuator and penetrating member, is then used to channel fluid from a source, such as a syringe, into the lumen for delivery of medication or other treatments. The side port which accesses the inner lumen of the penetrating member may also enable bodily fluids or tissues to be extracted by applying suction.

Other additional features include embodiments that enable delivery or removal of fluids through a side mounted syringe that oscillates back and forth relative to the handpiece body where the driving actuator is coupled to the syringe and supplies the oscillation or vibration to the syringe. A coupling mechanism is attached to the syringe that enables reversible attachment of a penetrating member (or to a separate device that already has a penetrating member attached to it). This embodiment includes a means to easily accomplish movement of the syringe plunger to a forward or backward position for delivery or removal of bodily fluids, tissues, nutrients, medicines, or therapies.

With regard to driving actuators in the handpiece that exhibit resonant behavior, such as the VCM actuator (discussed in embodiments presented below), the invention includes a set of methods by which to optimally operate the device in order to achieve desired oscillation amplitudes throughout the insertion of a penetrating member into target tissues. The resonant peak in the displacement versus frequency response of the driving actuator is influenced greatly by the loading from the tissue that interacts with the penetrating member. The reason for the change in the frequency response is because the penetrating member experiences frictional, inertial, and elastic forces that interact with the driving actuator, and the overall system exhibits an altered frequency response. By operating the device at some frequency above the resonant frequency of the driving actuator in air (for example >⅓ octave, but more optimally near ½ octave), the reciprocating motion can be maintained with very little, if any, damping for penetration of many tissue types.

Alternatively a feedback loop can be constructed by employing a displacement sensor (such as, but not limited to, a linear variable differential transformer (LVDT) to continually monitor displacement and a controller that can continually adjust the operating frequency to keep it near the actual resonance frequency of the coupled system (tissue and driving actuator, coupled via penetrating member). By attempting to keep the operating frequency near resonance of the coupled system, power requirements of the device are greatly reduced. Keeping the system at resonance also mitigates the need to 'overdrive' the system, i.e., drive at a displacement or frequency greater than needed initially, which can contribute to unnecessary heating. The monitoring of the frequency and displacement of the system can also be used to signal the transducer to stop vibration when penetration of the desired tissue is complete.

Another feedback-based method of maintaining near constant oscillatory displacement amplitude during insertion of the penetrating member into variety of tissues, utilizes current control. With this method, the current amplitude supplied to the driving actuator is increased to overcome the damping effects of tissue on the reciprocating penetration member. Again, a displacement sensor can be employed to continually monitor displacement and adjust current amplitude to achieve the target displacement magnitude. Additional methods may deploy a combination of frequency and current control methods by which to maintain displacement. Other methods may not employ feedback but simply anticipate the loading effect of the target tissue and set the operating frequency or current such that optimal displacement amplitude is achieved at some point during the course of tissue penetration. The system may be off resonance when no load is encountered by the penetrating member. However, when the penetrating member penetrates tissue the loading causes the resonance of the system to move closer to the driving frequency such that no adjustments to the driving actuator are needed. In some instances the resonance of the system may be at the driving frequency in the loaded condition. In other arrangements, the driving actuator may be adjusted so that it is on resonance when in a loaded state, and is off resonance during no load conditions. In yet other arrangements, the operating frequency is not at a resonance frequency when in the no load condition, but the operating frequency is closer to the resonance frequency, as compared to the no load resonance frequency, when in the load condition.

The handheld device of the present invention may require an electrical power signal to excite an internal actuator. Upon excitation by the electrical signal, the driving actuator converts the signal into mechanical energy that results in oscillating motion of the penetrating member, such as an attached needle, lancet, epidural catheter, biopsy instrument, or vascular entry instrument.

Additionally the invention with specific control electronics will provide reduction of force as the penetrating member is inserted and/or retracted from the body.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 1B is a cross-sectional view that illustrates the magnet assembly of the driving actuator (VCM);

FIG. 1C is a cross-sectional view that illustrates the VCM of FIG. 1A;

FIG. 2A is a side view of the driving actuator handpiece with a LUER-hub style penetrating member attached;

FIG. 2B is a close up view of the LUER-hub style penetrating member coupled to the distal tip of driving actuator handpiece;

FIG. 7B is a side view of the embodiment of FIG. 7A that shows the guide shaft and coupled plunger in a forward position;

FIG. 7C is a side view of an embodiment of FIG. 7A that shows the guide shaft and coupled syringe plunger in a backward position;

FIG. 8A is a side view of an embodiment utilizing a geared slider for movement of the coupled syringe plunger and located in a forward position;

FIG. 8B is a side view of an embodiment utilizing a geared slider for movement of the coupled syringe plunger and located in a back position;

FIG. 8C is a cross-sectional view of an embodiment of FIG. 8A and FIG. 8B utilizing a geared slider to move the coupled syringe plunger forward and back;

FIG. 11 is a graphic containing plots of displacement (oscillation amplitude) during the course of insertion of a penetrating member into tissue with driving actuator set to provide different displacement frequency and amplitude levels;

Figure 1A:
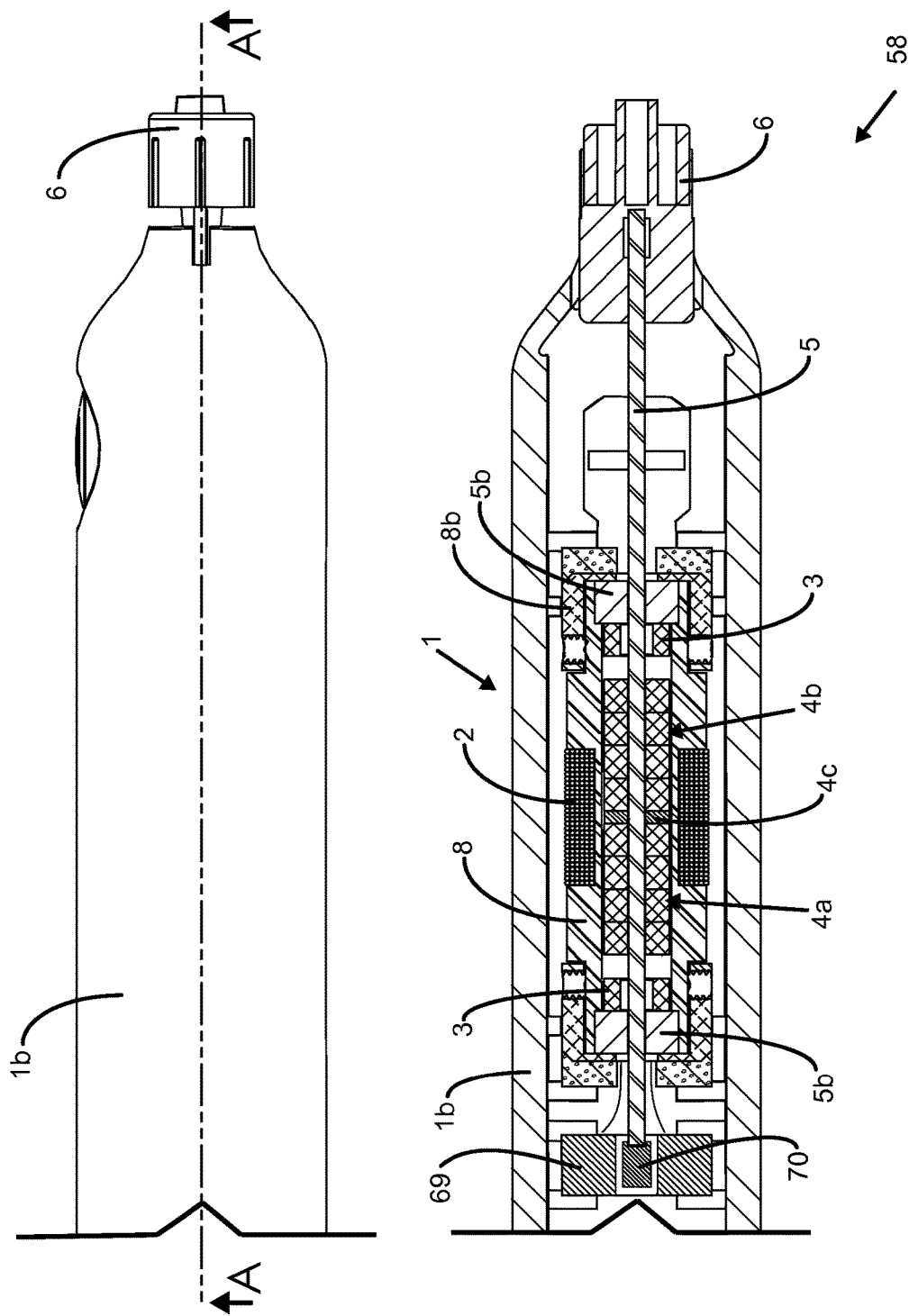
FIG. 1A is a cross-sectional view of the preferred embodiment of the driving actuator handpiece utilizing a reciprocating VCM and LVDT sensor.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The preferred embodiments of the present invention are illustrated in FIGS. 1A-13 with the numerals referring to like and corresponding parts. For purposes of describing relative configuration of various elements of the invention, the terms "distal", "distally", "proximal" or "proximally" are not defined so narrowly as to mean a particular rigid direction, but, rather, are used as placeholders to define relative locations which shall be defined in context with the attached drawings and reference numerals. A listing of the various reference labels are provided at the end of this Specification. In addition, as previously stated U.S. Pat. Nos. 8,043,229 and 8,328,738) were incorporated by reference into the present application and include various embodiments.

The effectiveness of the invention as described, utilizes high-speed oscillatory motion to reduce forces associated with inserting a penetrating member through tissue or materials found within the body. Essentially, when tissue is penetrated by a high speed operation of a penetrating member portion of the device, such as a needle, the force required for entry as well as the amount of tissue deformation is reduced. A reciprocating penetrating member takes advantage of properties of high speed needle insertion, but because the displacement during each oscillatory cycle is small (typically <1 mm) it still enables the ability to maneuver or control the needle, such as to follow a non-linear insertion path or to manual advance the needle to a precise target.

To exploit the reduction of force effect, the medical device of the present invention is designed such that the penetrating distal tip portion attains a short travel distance or displacement at high speed, axially reciprocating at a specified frequency. Utilizing the various device configurations as described in the aforementioned embodiments, it has been determined that the reciprocating motion of the penetrating member may include a displacement for the motor shaft of the driving actuator between 0.1-2 mm, more preferably between 0.5-1.5 mm, at a frequency of between 50-500 Hz, but most preferably at 75-200 Hz for insertion into soft tissues within the body. This motion is caused by the penetrating member 10 being attached to a voice coil motor operated with an AC power signal.

Generally, any type of motor comprising an actuator assembly, further comprising a voice coil motor (VCM), or solenoid, or any other translational motion device, including piezoelectric actuators, would serve as a driving actuator and also fall within the spirit and scope of the invention.

FIG. 1A depicts an embodiment of the present invention using a linear VCM as the mechanism for the driving actuator 1. FIG. 1A through 3C show cross-sectional view A-A 58, cross-sectional view of the magnet assembly 4, and a detail cross-sectional view of the VCM. A VCM creates low frequency reciprocating motion. In particular, when an alternating electric current is applied through the conducting voice coil 2, the result is a Lorentz Force in a direction defined by a function of the cross-product between the direction of current delivered by the power cable 7 (see FIG. 5) to the voice coil 2 and magnetic field vectors of the magnet arrays 4a and 4b. The two magnet arrays, 4a and 4b, have equal and opposing magnetic polarity vectors and are separated by a pole piece 4c. Together, the magnet arrays 4a, 4b, and pole piece 4c make up the magnet assembly 4. By alternating the direction of the current in the voice coil 2, a sinusoidal alternating force is applied to the magnet assembly 4 resulting in a reciprocating motion of the motor shaft 5 relative to the VCM body 8 which is seated inside the driving actuator handpiece body 1b. The VCM body 8 may be constructed of metal or of plastic with a low coefficient of friction. Delrin is a preferred material choice. The motor shaft bearings 5b provide supplemental friction reduction and help to ensure the motor shaft movement is directed solely in the axial direction (coaxial with the VCM body 8). The reciprocating motor shaft 5 communicates this motion to a keyed coupler 6 and attached penetrating member 10 (see FIG. 2A). The penetrating member 10 may be a hypodermic needle, a solid lancet, or other sharp and may be bonded to a hub 11 (see FIG. 2A) such as, but not limited to a LUER-slip or LUER-lok style. FIG. 2B depicts a close up view of the penetrating member 10 attached via a bonded hub 11 to the keyed coupler 6. The tip of the penetrating member 10 may have a bevel end 12 to increase sharpness.

Referring again to FIG. 1A, in all of the voice coil actuator configurations described, opposite polarity centering magnets 3 may be used to limit and control certain dynamic aspects of the driving actuator 1. At least one centering magnet 3 is located inside the VCM body 8 at each end. The centering magnets 3 have a same inward facing magnetic polarity as the outward facing polarity of the magnet assemblies 4a and 4b; the VCM end caps 8b keep the centering magnets 3 held in place against the repelling force. The opposition of magnetic forces (between centering magnets 3 and magnet assembly 4) acts to keep the magnet assembly centered at the midpoint of the VCM body 8. The magnets are placed at a certain distance from the ends of the magnet arrays 4a and 4b so that they are forced back toward center following peak displacement, but far enough away that no physical contact is made during oscillations. As with other voice coil embodiments using coils, the basic principle of actuation is caused by a time varying magnetic field created inside a solenoidal voice coil 2 when AC current flows in the coil wire, delivered via the power cable 7. The time varying magnetic field acts on the magnet arrays 4a and 4b, each a set of very strong permanent magnets. The entire magnet assembly 4, which is rigidly attached to the motor shaft 5, oscillates back and forth through the voice coil 2. The centering magnets 3 absorb and release energy at each cycle, helping to amplify the oscillating motion experienced by the penetrating member 10 (shown in FIGS. 2A and 2B). The resonant properties of the device can be optimized by magnet selection, number of coil turns in the voice coil 2, mass of the motor shaft 5, and by the elimination of frictional losses as much as possible (e.g. between the magnet assembly 4 and VCM body 8, or between the motor shaft 5 and motor shaft bearings 5b). Furthermore, performance can be optimized by adjusting the strength of the repelling force between the ends of the magnet arrays 4a and 4b and the opposing polarity centering magnets 3, thus modulating the stiffness and overall frequency response of the system. Friction is further eliminated by utilizing a ring style magnet for the centering magnets 3 whose inner diameter is sufficiently larger than the outer diameter of the drive shaft 5. Most application embodiments will require the magnets 3, 4a, and 4c to be made of a Neodymium-Iron-Boron (NdFeB) composition. However other compositions such as, but not limited to Samarium-Cobalt (SmCo), Alnico (AlNiCoCuFe), Strontium Ferrite (SrFeO), or Barium Ferrite (BaFeO) could be used. Slightly weaker magnets could be more optimal in some embodiments, such as a case where the physical size of the system is relatively small and strong magnets would be too powerful.

Feedback means via LVDT 69 and LVDT core 70 can be implemented to monitor oscillatory displacement magnitude, oscillatory frequency, and displacement magnitude from center position. Oscillatory displacement magnitude can be utilized as electromechanical feedback for ensuring the motor shaft 5 is displacing optimally and also potentially can provide a signal that triggers an auto-shut of mechanism. Additionally the LVDT 69 and LVDT core 70 can be used as a force sensor by monitoring the oscillatory center position and comparing it to the unloaded center position. The displacement from center position can be calibrated to relate to a force, since the restoring force provided by the centering magnets 3 increases in proportion to the displacement. This information can be relayed to the operator and/or used as an operating state change trigger.

In some embodiments where larger displacements are desired or a lower resonant frequency is needed, the function of the centering magnets 3 may be replaced with springs, elastic material, and may include a means to dynamically modulate the stiffness of the restoring force or to implement non-symmetric centering forces so that when the penetrating member experiences force from the tissue, the magnet assembly 4 would be located more centrally within the VCM body 8.

One aspect of performing procedures correctly is a manner in which to hold the bevel end (12 in FIG. 2B) of the penetrating member (10 in FIGS. 2A and 2B) rotationally stable. For example, during venipunctures for medication delivery, blood sampling, or for catheterization, a clinician will attempt to locate the tip of a small needle into the center of the vessel. Whether using a lancet or hypodermic needle, the standard technique is to ensure the bevel end (12 in FIG. 2B) of the penetrating member (10 in 2A and FIG. 2B) is "facing up" throughout the penetration event. This is generally not a problem while holding the needle directly in the fingers but needs to be taken into account when the needle is attached to the driving actuator (1 in FIG. 1A). Since the moving magnet assembly (4 in FIG. 1A) does not require leads to be run to the moving part of the motor, as is the case for moving coil actuators, the motor shaft (5 in FIG. 1A) is generally free to rotate within the VCM body (8 in FIG. 1A) meaning that the attached keyed coupler 6 that receives the hub 11 rotates freely. This minimizes frictional losses, but poses a problem for connecting a beveled penetrating member (10 in 2A and FIG. 2B) to the end of the motor shaft (5 in FIG. 1A) because the bevel is not rotationally stable throughout the penetration process. Using springs as the restoring force for centering the magnet assembly (4 in FIG. 1A), supplies some rotationally resistive forces.

Figure 3A:
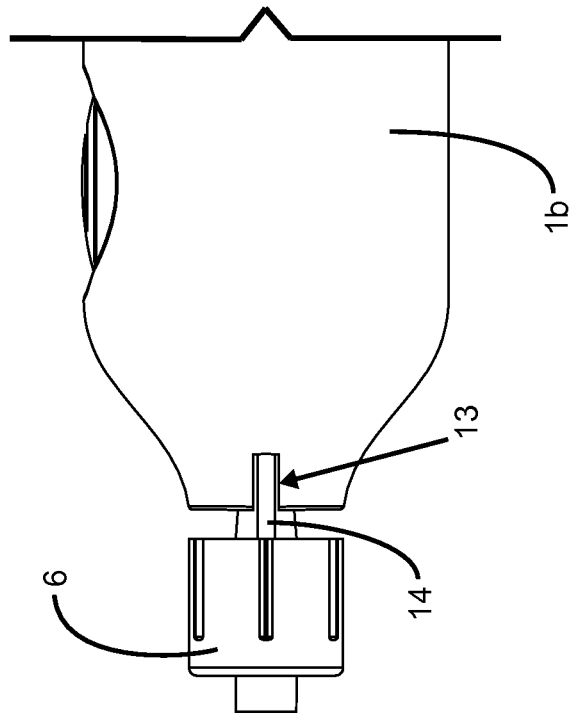
FIG. 3A is a perspective view of the keyed coupler at the distal end of driving actuator handpiece which restricts rotational movement of the attached penetrating member.
Figure 3B:
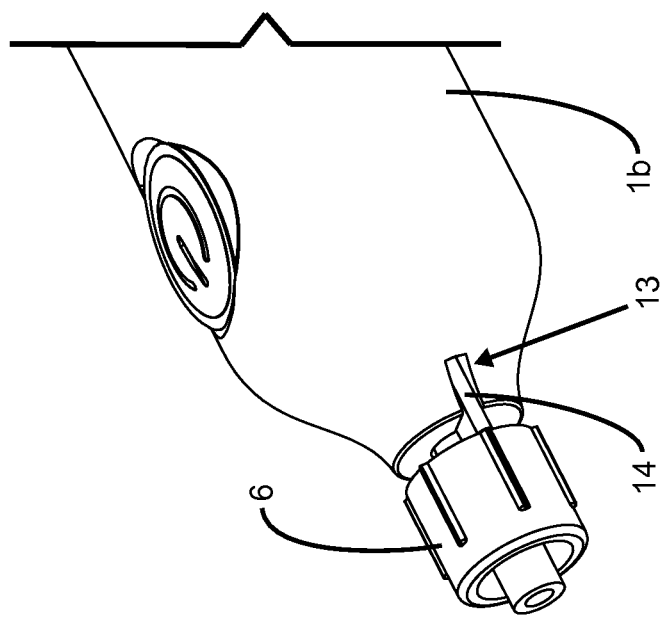
FIG. 3B is a complete side view of the LUER compatible keyed coupler showing the space (keyway) allowed around the tabs (keys) of the coupler.
Figure 3D:
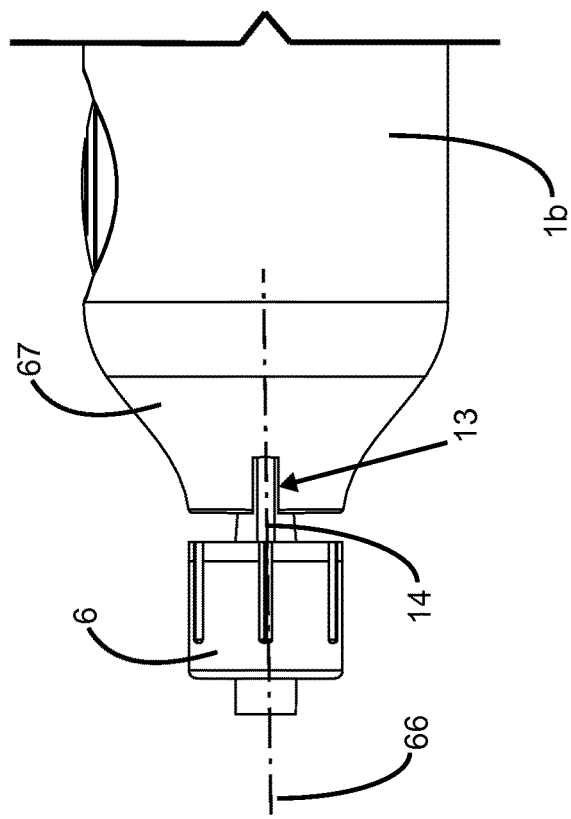
FIG. 3D is a complete side view of the LUER compatible keyed coupler showing the space (keyway) allowed around the tabs (keys) of the coupler within the rotating keyway head.
Figure 3C:
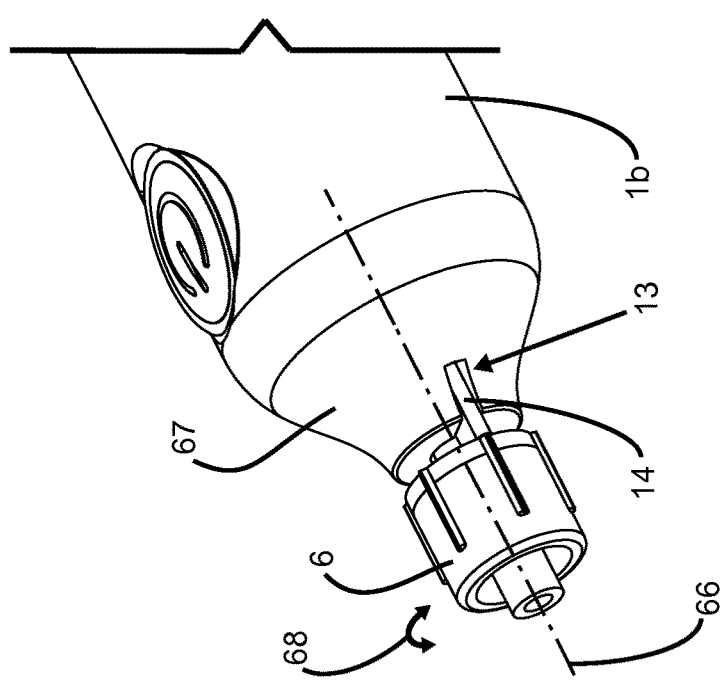
FIG. 3C is a perspective view of the keyed coupler and a rotating keyway head at the distal end of the driving actuator handpiece which provides controlled rotational movement while still allowing axial motion of the attached penetrating member.

FIG. 3A presents one approach to restrict axial rotation of penetrating member (10 in FIG. 1C) when attached to the shaft (5 in FIG. 1A). A keyed coupler 6 with side tabs to serve as keys 14 is implemented in conjunction with keyway 13 formed by slots in the distal end of the driving actuator handpiece body 1b. The keyed coupler 6 is permanently fixed to the shaft 5 to allow reversible connection, for instance, to LUER-Lok needle hubs, but could be adapted for a range of other attachment schemes. FIG. 3B provides a lateral view of the coupling end of the driving actuator highlighting the keyed coupler 6 and surrounding keyway 13. Sufficient clearance between the keyway 13 slots on either side of the handpiece body 1*b* and the keys 14 is made to prevent frictional forces from damping out the oscillating motion. Friction can further be reduced between the keys 14 and keyway 13 by coatings and/or lining opposing surfaces with low friction materials. In an alternate embodiment depicted in FIGS. 3C and 3D, the front of the device incorporates a rotating keyway head 67 which can undergo controlled rotating motion 68 about a central axis of rotation 66. The motion may be produced by coupling the rotating keyway head 67, to rotational motor (not shown) such as a servomotor. This configuration would decouple the rotational and axial motions so that they can be controlled independently. The combined rotational and axial motions may further aid insertion especially into tougher tissues.

Figure 4:
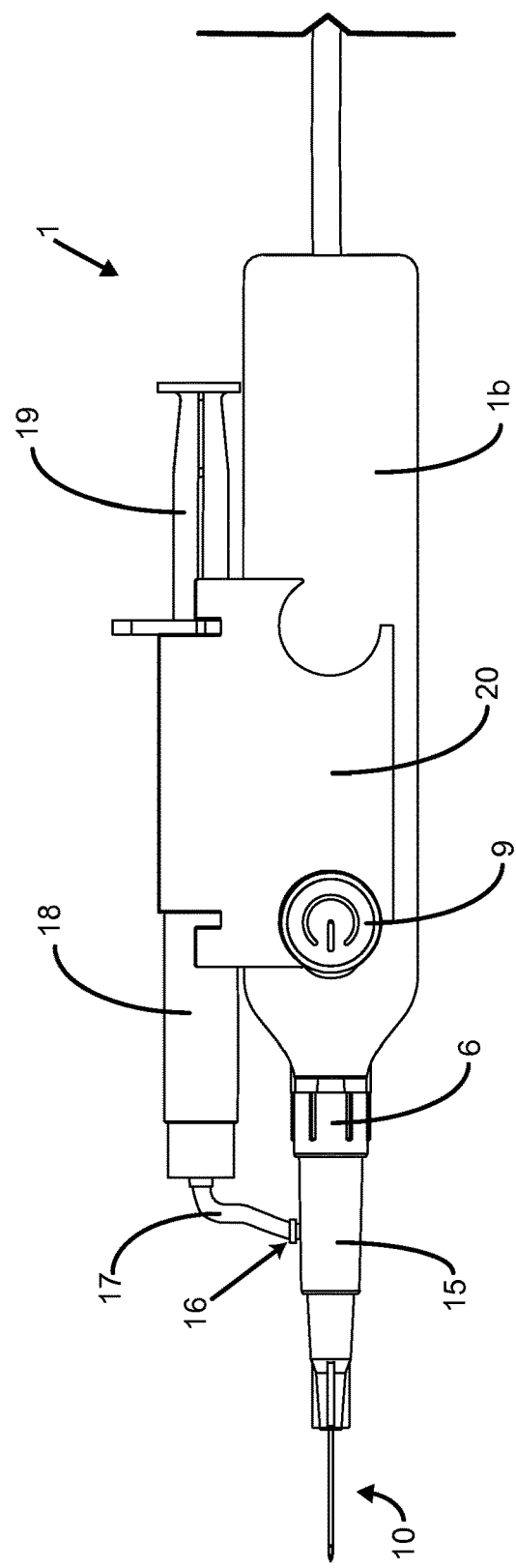
FIG. 4 is a top plane view of the driving actuator handpiece with a mounted syringe connected to the side port of the LUER-hub of penetrating member for removal or injection of fluids.

FIG. 4 shows an alternate embodiment of the device which incorporates a side port 16 which provides access to the inner lumen of the penetrating member 10. A segment of compliant tubing 17 may link the side port 16 to a fluid delivery source such as a syringe. The syringe body 18 can be reversibly attached to the driving actuator handpiece body 1*b* by a syringe coupling bracket 20. When the plunger 19 is pressed into the syringe body 18, fluid (such as medication, fluids, or vaccines) may be delivered into the body via an inner lumen of the penetrating member 10. In other applications, this or a similar embodiment would allow for extraction of fluids, tissue, or other materials (such as blood, fluid, or cells) into the syringe body 18 by pulling back on the syringe plunger handle 19 to create a negative pressure inside the compliant tubing 17 and inner lumen of the penetrating member 10. The compliant tubing 17 is sufficiently flexible so as not to impede the axially-directed oscillatory motion of the keyed coupler 6 or attached penetrating member 10. Obtaining inner lumen access may be implemented by attaching an intervening coupling piece with side port 15 between the fixed hub of the penetrating member 10 and the keyed coupler 6 as shown in FIG. 4, it could also be implemented by incorporating a side port directly into the fixed hub of the penetrating member 10. Further, the compliant tubing 17 could either be permanently integrated into the hub or coupling piece, or be an independent component with end fittings that reversibly mate with the side port 16 and syringe body 18. Other similar embodiments are envisioned that include a mounted syringe or other method of fluid injection into a side port 16, including gun-style injectors of vaccines and other medications for care and treatment of livestock in agricultural settings.

Figure 5:
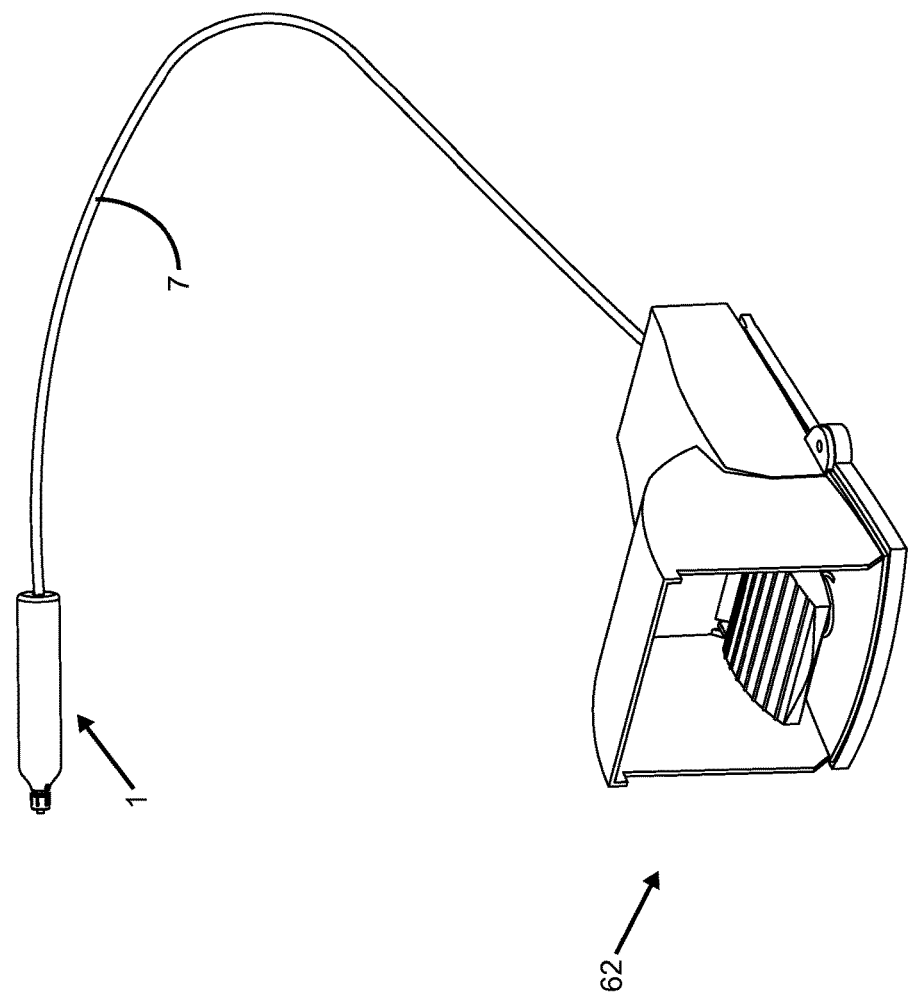
FIG. 5 is a perspective view of the driving actuator handpiece with an incorporated foot switch for initiating and terminating power to the driving actuator.

FIG. 5 presents another approach through use of a foot switch 62, to initialize and de-initialize power supplied to the driving actuator 1 via the power cable 7. This approach can also incorporate both the foot switch 62 and the power button 9 (not shown) for the option of initializing and de-initializing power to the driving actuator 1.

Figure 6A:
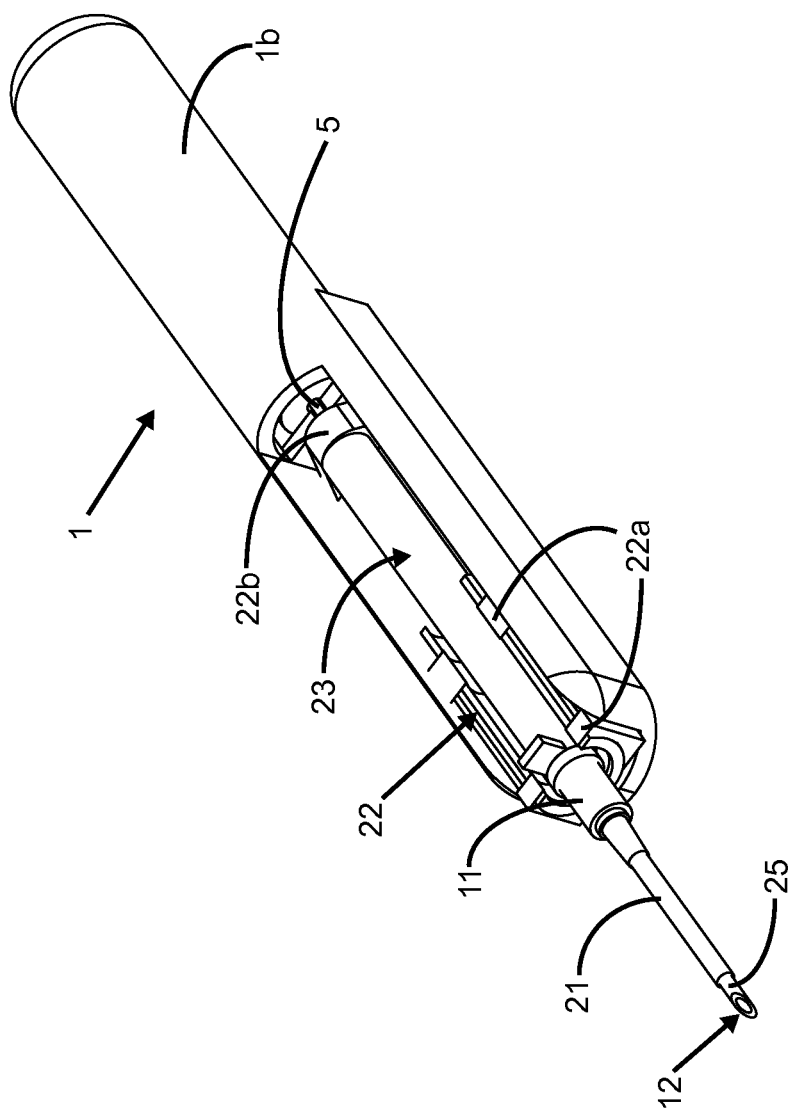
FIG. 6A is a view of an embodiment of the driving actuator handpiece with an inline coupling sled attachment dipped to a safety IV device for the purpose of providing reciprocating motion to penetrating member.
Figures 6B, 6C:
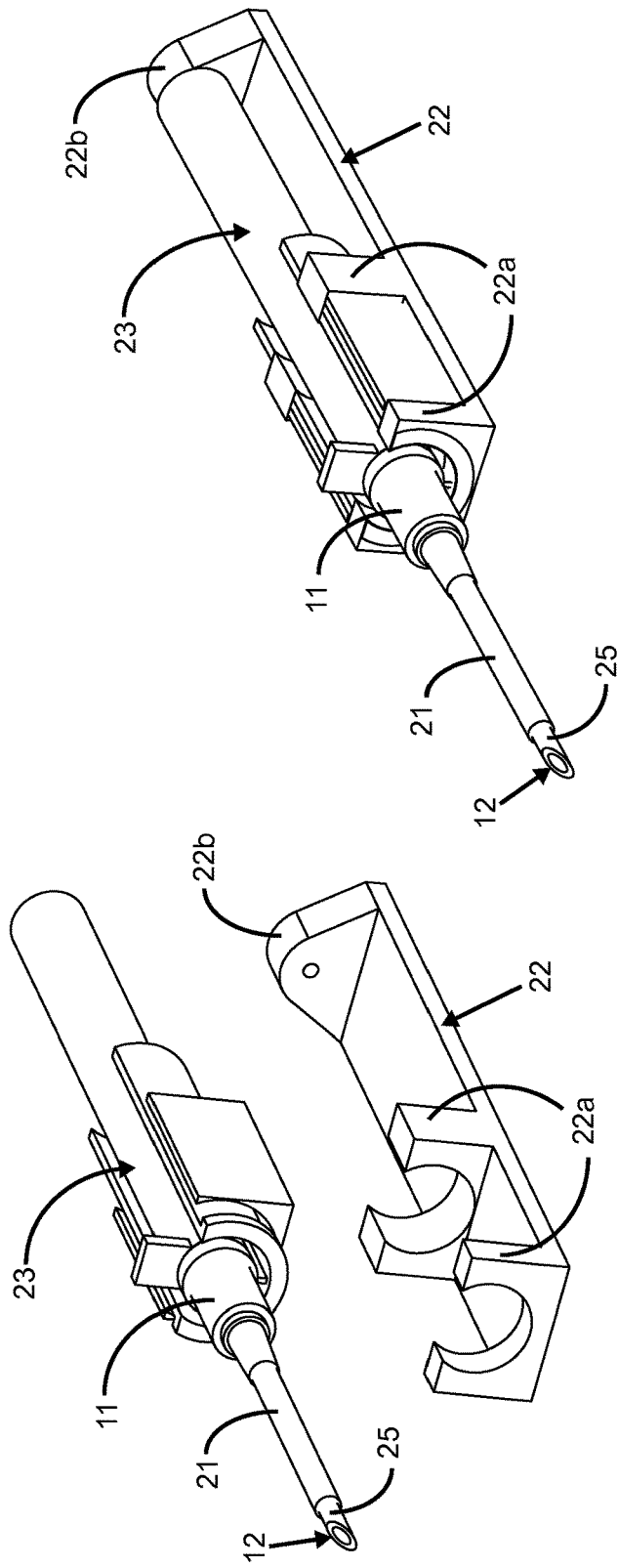
FIG. 6B shows an isolated view demonstrating safety IV device attachment to coupling sled (driving actuator handpiece not shown)
FIG. 6C is a perspective view of the safety IV device after attached to the coupling sled.
Figure 6D:
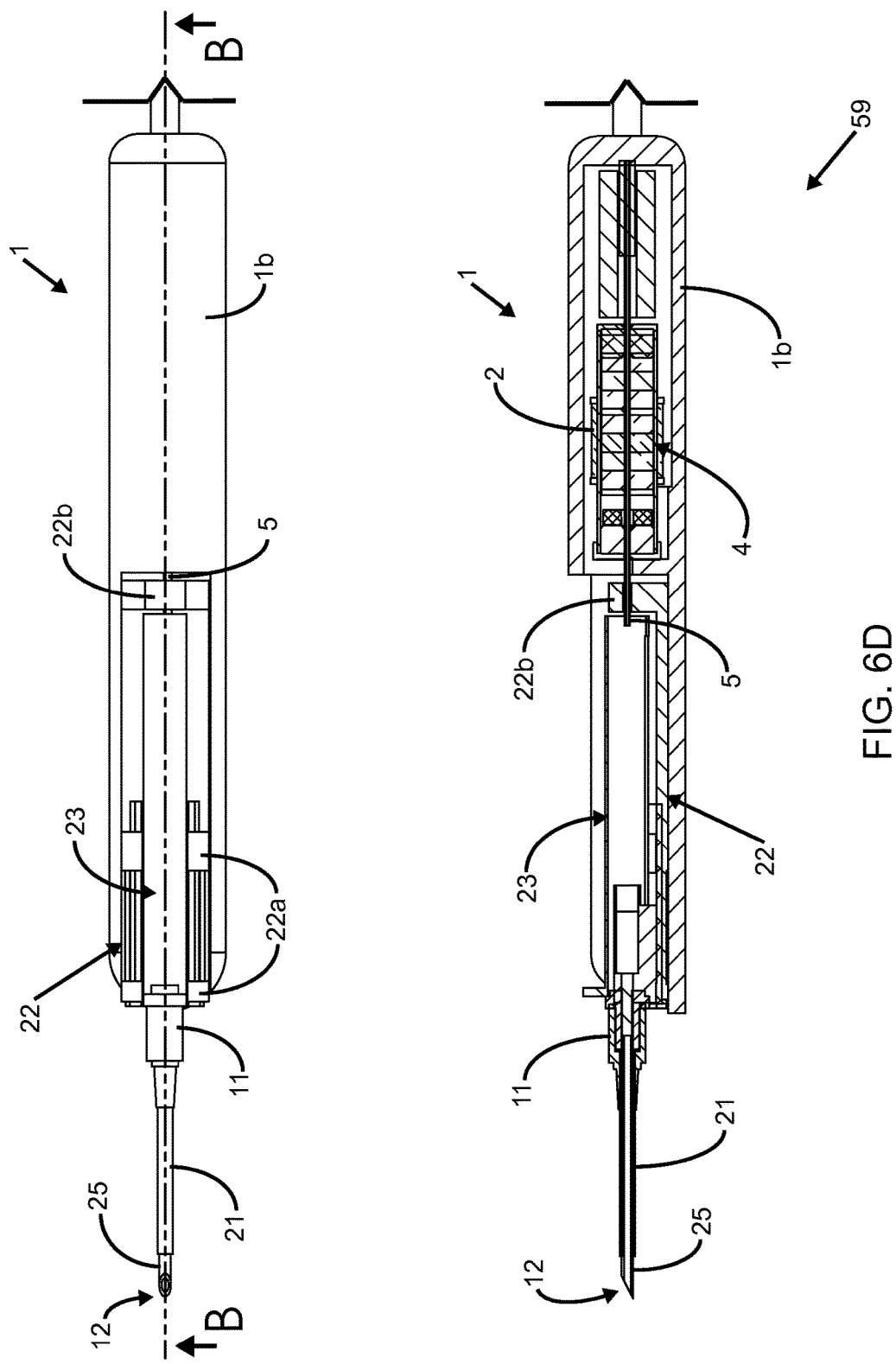
FIG. 6D is a cross-sectional view that illustrates the driving actuator handpiece utilizing a reciprocating VCM that incorporates a coupling sled attachment clipped to a safety IV device.

In another embodiment as shown in FIG. 6A-6D, the driving actuator 1 is used to aid the placement of an IV catheter into a vessel in order to have long-term access to the vascular system. This could be done by using a safety IV device 23 or any other device with an attached penetrating member that does not have a hub that can be easily attached to the driving actuator 1. In this case the driving actuator 1 must be adapted to couple the motor shaft 5 to the body of the penetrating device. This requires the coupling to occur more from the lateral aspect of the device to be oscillated, rather than at the proximal end because a hub is not present or is inaccessible. To accomplish this, a coupling sled 22 (shown in more detail in FIGS. 6B and 6C) that has clips 22*a* that are geometrically compatible with specific penetrating devices is used to attach the penetrating device to the reciprocating motor shaft 5. The proximal end of coupling sled 22*b* connects to the motor shaft 5 which is forced back and forth by the interaction of the magnet assembly 4 and the magnetic field generated by electric current flowing through the voice coil 2. The coupling sled 22 is supported and guided by the structure of the handpiece body 1*b*. During a vascular access procedure, for instance, the driving actuator 1 delivers oscillatory motion to the IV penetrating member 25 to aid tissue penetration. When the bevel end 12 is inside the vessel to be catheterized, the IV catheter 21 is slid off the penetrating member 25 and into the vessel. The penetrating member 25 is then retracted into the body of the safety IV device 23, which can be removed from the clips 22*a* of the coupling sled and discarded. In FIG. 6C, the attachment of a safety IV device 23 to the coupling sled 22 is shown in isolation.

To ensure that the oscillatory motion is not over damped by the coupling sled 22, the moving mechanism must have sufficiently small resistance coefficient. In one embodiment the coupling sled is guided solely by the shape of the handpiece body (1*b* in FIG. 6D, section B-B 59). Here the interfacing surfaces are comprised of two materials having a low coefficient of friction. In another embodiment the coupling sled may be guided by for instance a linear ball-bearing guide rail. In another embodiment the coupling sled is capable of attaching to one or more linear round shafts utilizing bearings or material surfaces with low coefficient of friction to minimize sliding resistance.

Figure 7A:
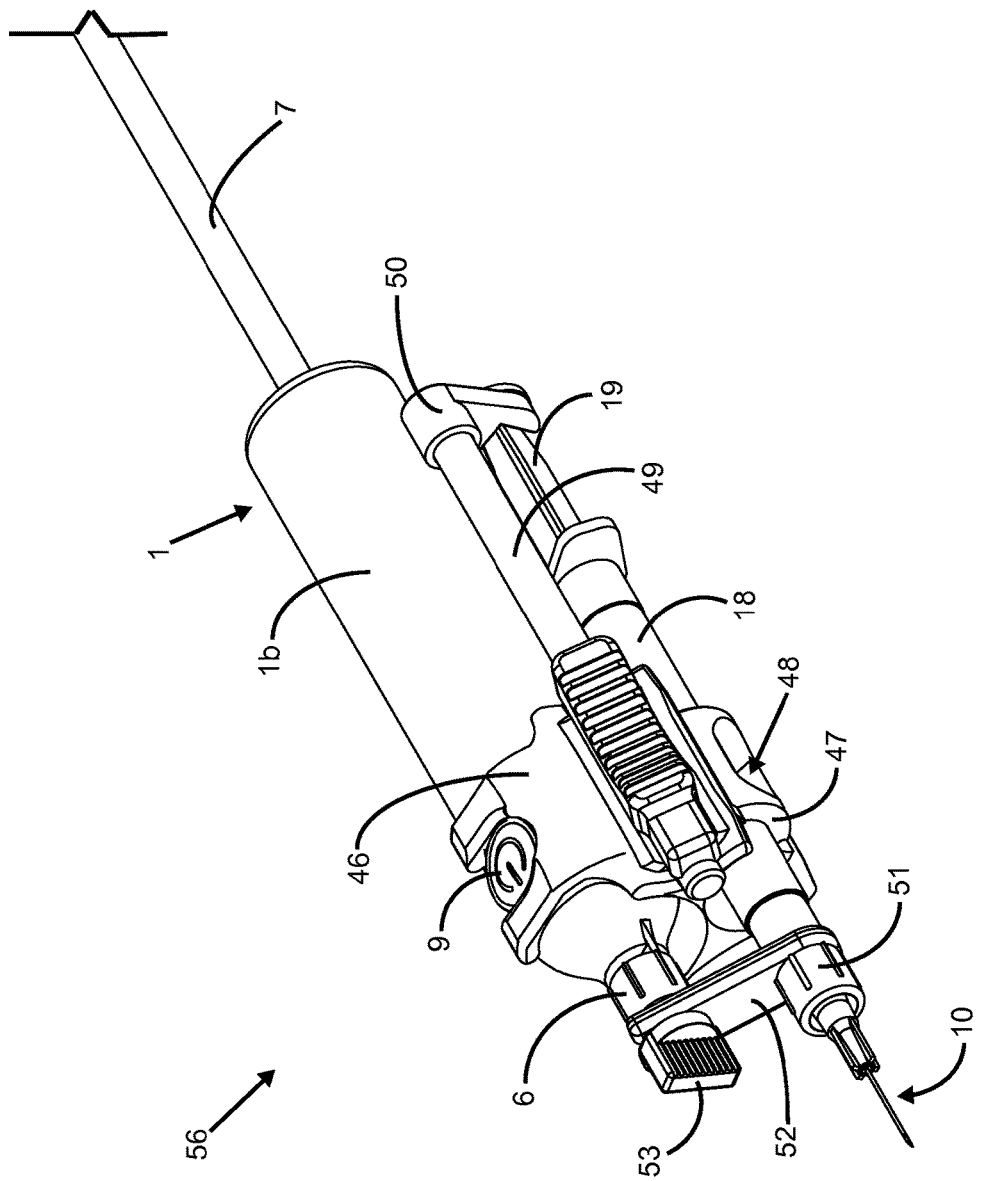
FIG. 7A is a perspective view of an embodiment of the driving actuator handpiece with a side mounted syringe that is attached to the driving actuator to provide axially-directed oscillatory motion to the syringe and coupled penetrating member.

FIG. 7A-7C shows an alternate embodiment, slider device 56, which incorporates a fluid delivery source, such as a syringe, actuated by a driving actuator 1. Power is initialized and de-initialized by the power button 9 and supplied to the driving actuator 1 via the power cable 7. This could also be done with use of a foot switch 62 (as shown in FIG. 5). The actuation is transferred from the driving actuator 1 to the syringe via a keyed coupler 6 and a syringe clip 52. The syringe clip is mechanically attached to the keyed coupler 6 by use of a LUER-Lok coupling member (such as a thumb coupler 53). The syringe clip 52 pivots around the thumb coupler 53 360° to allow for quick attachment and detachment to the syringe coupler 51 which provides a mechanical attachment to both the syringe body 18 and the penetrating member 10. The syringe body 18 can be reversibly attached to the driving actuator handpiece body 1*b* by a handpiece clip 46. The syringe body 18 could be held in place using an interchangeable syringe adapter 47 that is inserted into a cavity of the handpiece clip 46, allowing for different sizes of the syringe body 18 and allowing for precise linear movement of the syringe body 18 within the syringe adapter 47. A means of visibility such as the syringe adapter window 48 is used to allow for clear visibility of the level of fluid (such as medication, fluids, or vaccines) within the syringe. When the plunger 19 is pressed into the syringe body 18, fluid may be delivered into the body via an inner lumen of the penetrating member 10 that is attached to the syringe body 18 through a syringe coupler 51. One-handed operation of the device can be achieved by allowing movement of the plunger 19 to be initiated through movement of the guide shaft 49 coupled to the plunger 19 through the guide shaft coupling 50. In other applications, this or a similar embodiment would allow for extraction of fluids, tissue, or other materials (such as blood, fluid, or cells) into the syringe body 18 by pulling back on the syringe plunger 19. A switch of the handpiece clip 46 may be located distal to the guide shaft coupling 50 and distal to some or all of the plunger 19. The switch of the handpiece clip 46 may be located adjacent the exterior handpiece body 1b and may allow for easier and more convenient actuation of the plunger 19 during use of the device.

FIG. 7B shows this embodiment with the guide shaft 49 pressing the plunger 19 to a forward position 63 following delivery of fluid contents (or the starting condition for fluid removal procedure). FIG. 7C shows this embodiment with the guide shaft 49 pulling the plunger 19 to a backward position 64 for the purpose of removing fluids (or the starting condition for fluid delivery procedure).

Figure 8D:
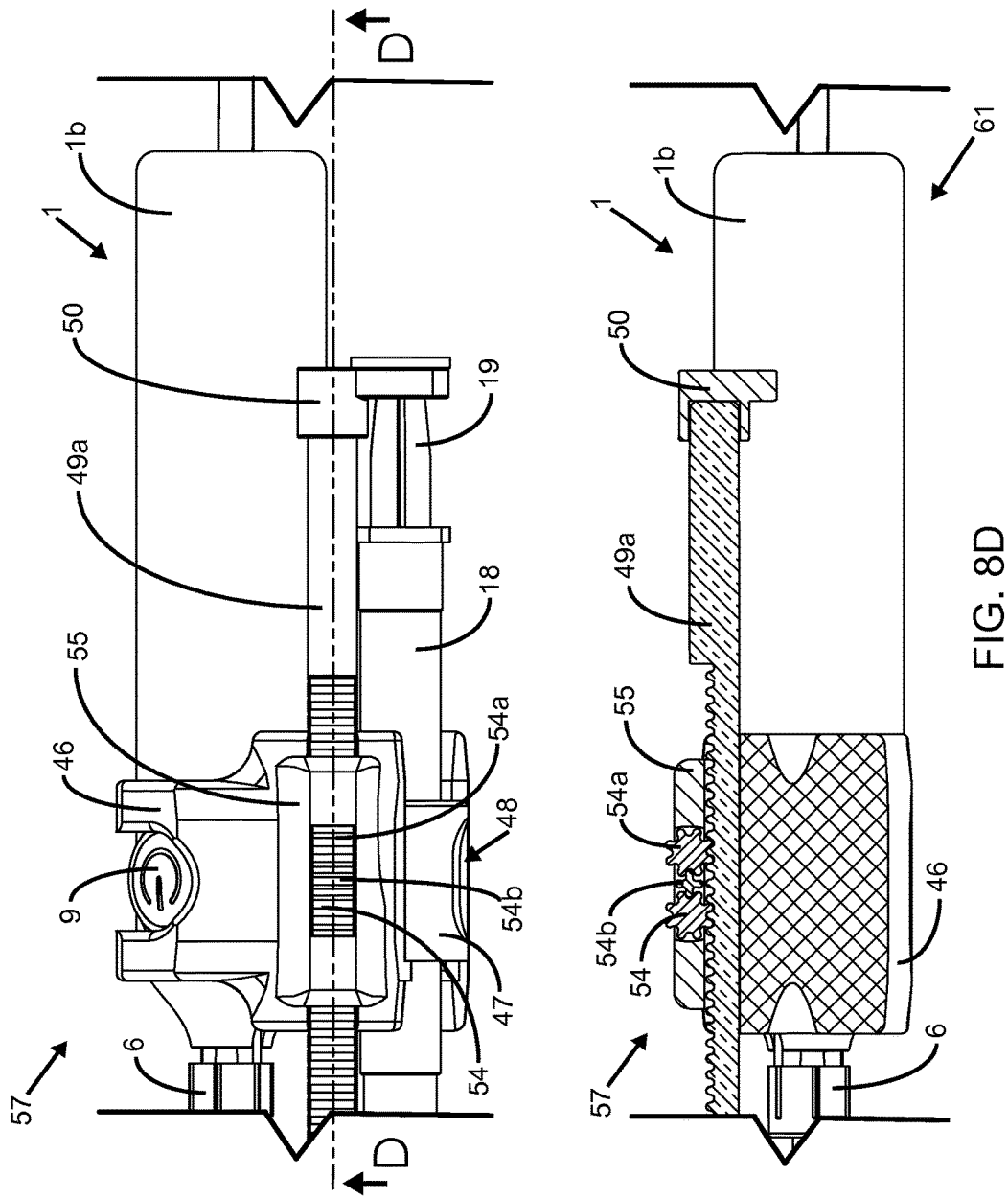
FIG. 8D is a cross-sectional view of an alternate embodiment utilizing a double geared slider to move the coupled syringe plunger forward and back.

FIG. 8A-8C shows an alternate embodiment of FIG. 7A, geared slider device 57, which incorporates a fluid delivery source, such as a syringe, actuated by a driving actuator 1. Power is initialized and de-initialized by the power button 9 and supplied to the driving actuator 1 via the power cable 7. This could also be done with use of a foot switch 62 (as shown in FIG. 5). The actuation is transferred from the driving actuator 1 to the syringe via a keyed coupler 6 and a syringe clip 52. The syringe clip is mechanically attached to the keyed coupler 6 by use of a LUER-Lok coupling member (such as a thumb coupler 53). The syringe clip 52 pivots around the thumb coupler 53 360° to allow for quick attachment and detachment to the syringe coupler 51 which provides the mechanical attachment to both the syringe body 18 and the penetrating member 10. The syringe body 18 can be reversibly attached to the driving actuator handpiece body 1b by a handpiece clip 46. The syringe body 18 could be held in place using an interchangeable syringe adapter 47 that is inserted into a cavity of the handpiece clip 46, allowing for different sizes of the syringe body 18 and allowing for controlled linear movement of the syringe body 18 within the syringe adapter 47. The plunger 19 may move in relation to the handpiece body 1b. A means of visibility such as the syringe adapter window 48 is used to allow for clear visibility of the level of fluid (such as medication, fluids, or vaccines) within the syringe. When the plunger 19 is pressed into the syringe body 18, fluid may be delivered into the body via an inner lumen of the penetrating member 10 that is attached to the syringe body 18 through a syringe coupler 51. Movement of the plunger 19 is initiated through movement of the geared guide shaft 49a and is coupled to the geared guide shaft 49a through the guide shaft coupling 50. A mechanical mechanism including but not limited to a drive gear 54 or a drive gear accompanied by another gear, drive gear two 54a, housed within the drive gear housing 55 can be used to drive the geared guide shaft 49a. The means of providing forward or backward motion to the drive gear 54 or drive gear two 54a is through human kinetic energy or electric energy converted to mechanical energy such as but not limited to a DC motor (not shown). In other applications, this or a similar embodiment would allow for extraction of fluids, tissue, or other materials (such as blood, fluid, or cells) into the syringe body 18 by pulling back on the syringe plunger 19. FIG. 8A shows this embodiment with the geared guide shaft 49a pressing the plunger 19 to a forward position 63 following delivery of fluid contents (or the starting condition for fluid removal procedure), FIG. 8B shows this embodiment with the geared guide shaft 49a pulling the plunger 19 to a backward position 64 for the purpose of removing fluids (or the starting condition for fluid delivery procedure). FIG. 8C shows the geared slider device 57 with the use of a drive gear 54 to move the plunger 19 to a forward position 63 and a back position 64 as shown in FIGS. 8A and 8B, FIG. 8D shows the geared slider device 57 with the use of a drive gear 54 and drive gear two 54a to move the plunger 19 to a forward position 63 and a back position 64 as shown in FIGS. 8A and 8B. If only one gear is turned, drive gear 54 or drive gear two 54a, the other will move simultaneously do to the idler gear 54b along with the interlocking teeth of the geared drive shaft 49a.

Figure 9:
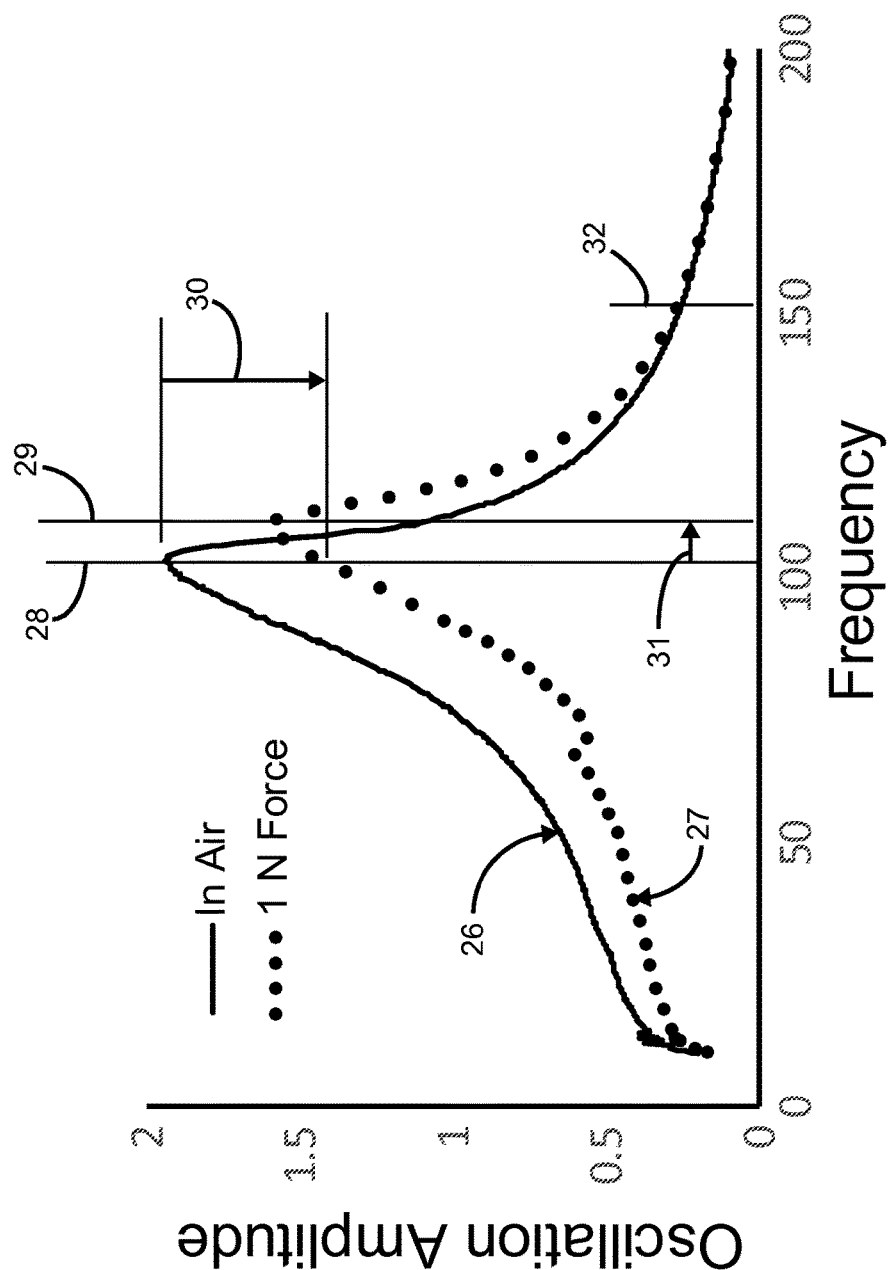
FIG. 9 is a graph showing typical displacement versus frequency behavior for VCM driving actuator in loaded and unloaded conditions.

FIG. 9 displays experimental data obtained with a VCM embodiment of the driving actuator (1 in FIG. 1A) which demonstrates the frequency response behavior of the device as an elastic axial force is applied to keyed coupler 6 (not shown). The frequency response of the driving actuator in air (non-loaded) 26 exhibits resonant behavior with a peak displacement occurring at the resonant frequency in air 28. After the application of a moderate axial load of 1 N (simulating typical forces encountered during penetration of a 25 G hypodermic needle into rat tail skin), the device resonant frequency shifts 31 according to the new frequency response of driving actuator with axial force applied 27 (1 N elastic load force, applied axially). If the device were for instance operated at the original resonant frequency in air 28 when axial load force is applied during the course of tissue penetration, then it would cause an upward resonant frequency shift 31 with a resultant oscillatory displacement damping 30 at original resonant frequency 28. One method to overcome this shortcoming is to choose a damping resistant operating frequency 32 that is significantly higher than the original resonant frequency in air 28. As shown by the plots in FIG. 9, the damping effect of axial load on the oscillatory displacement amplitude is minimal at this damping resistant operating frequency 32, as shown by the overlap of the frequency response curves (i.e., frequency response on driving actuator in air (non-loaded) 26 and frequency response of driving actuator with axial force applied (loaded) 27) above this frequency.

Another method of counteracting the oscillatory damping that is caused by the axial force applied to the penetrating member by the tissue is to employ feedback to adjust the operating frequency or current during the penetration. Two different approaches are now mentioned and illustrated with the aid of FIGS. 10A and 10B which show frequency response curves of a simulated 2nd order mass-spring-damper model with parameters chosen to match behavior comparable to driving actuator characterized in FIG. 9. The simulated frequency response in air 33 of a VCM-based driving actuator in air (non-loaded condition) has a resonant displacement peak in air 35 occurring at the resonant frequency in air 28. When the effect of elastic tissue interaction with the penetrating member is added to the model (as an increase in spring stiffness), the simulated frequency response in tissue 34 is shifted relative to the original simulated frequency response in air 33. The resonant displacement peak in tissue 37 occurs at a different, in this case higher, resonant frequency in tissue 71. The end result is a displacement in tissue at original resonant frequency 36 that is reduced because the resonant frequency in air 28 is different than the resonant frequency in tissue 71. In an embodiment employing a displacement sensor (e.g. LVDT) to monitor oscillatory displacement of the motor shaft 5 (not shown), the reduced displacement is sensed and the controller would adjust the operating frequency closer to the resonant frequency in tissue 71 so that the displacement would necessarily increase closer to the resonant displacement peak in tissue 37. By employing a feedback loop to continually adjust the operating frequency so that it is always near the current resonant frequency of the combined driving actuator-tissue system, power consumption of the device can be minimized.

Figure 10A:
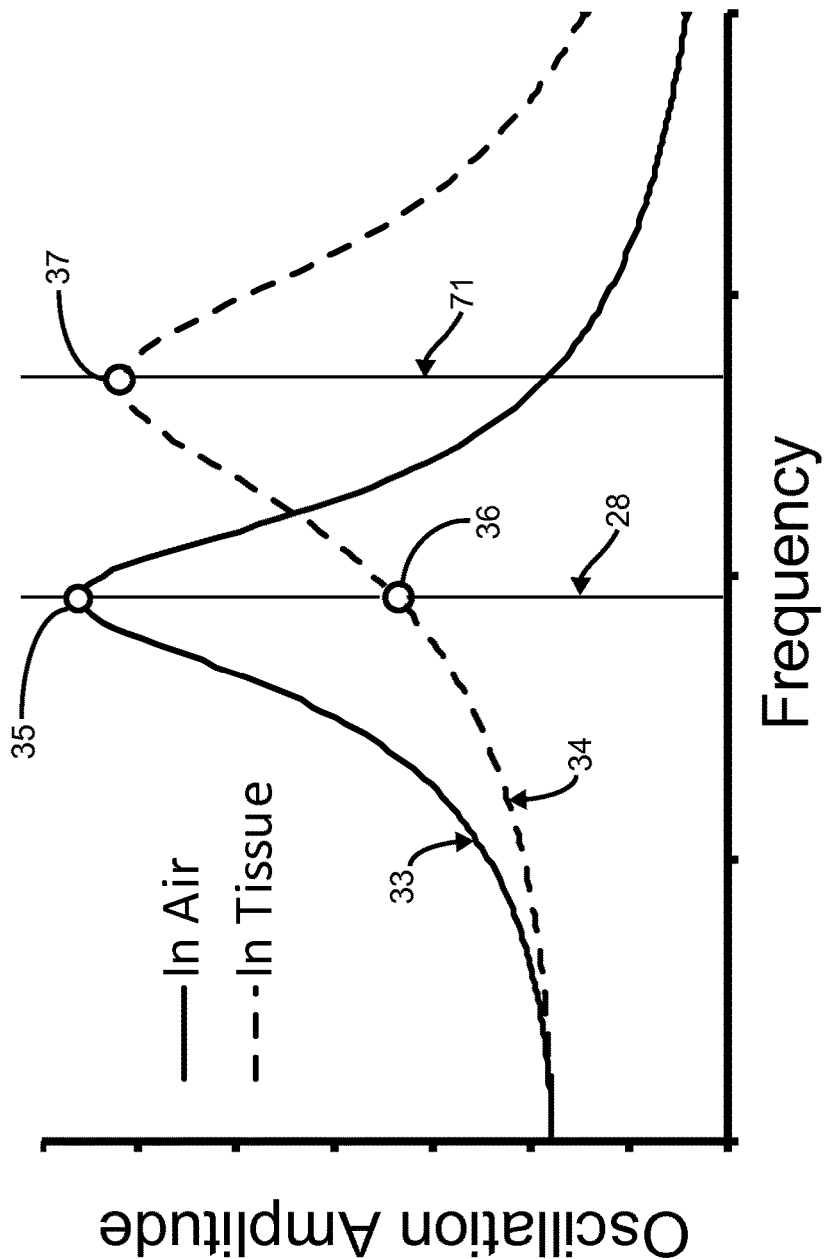
FIG. 10A is a graphic demonstration of frequency-based displacement control method for overcoming the damping effect of tissue during a tissue penetration event using the driving actuator.
Figure 10B:
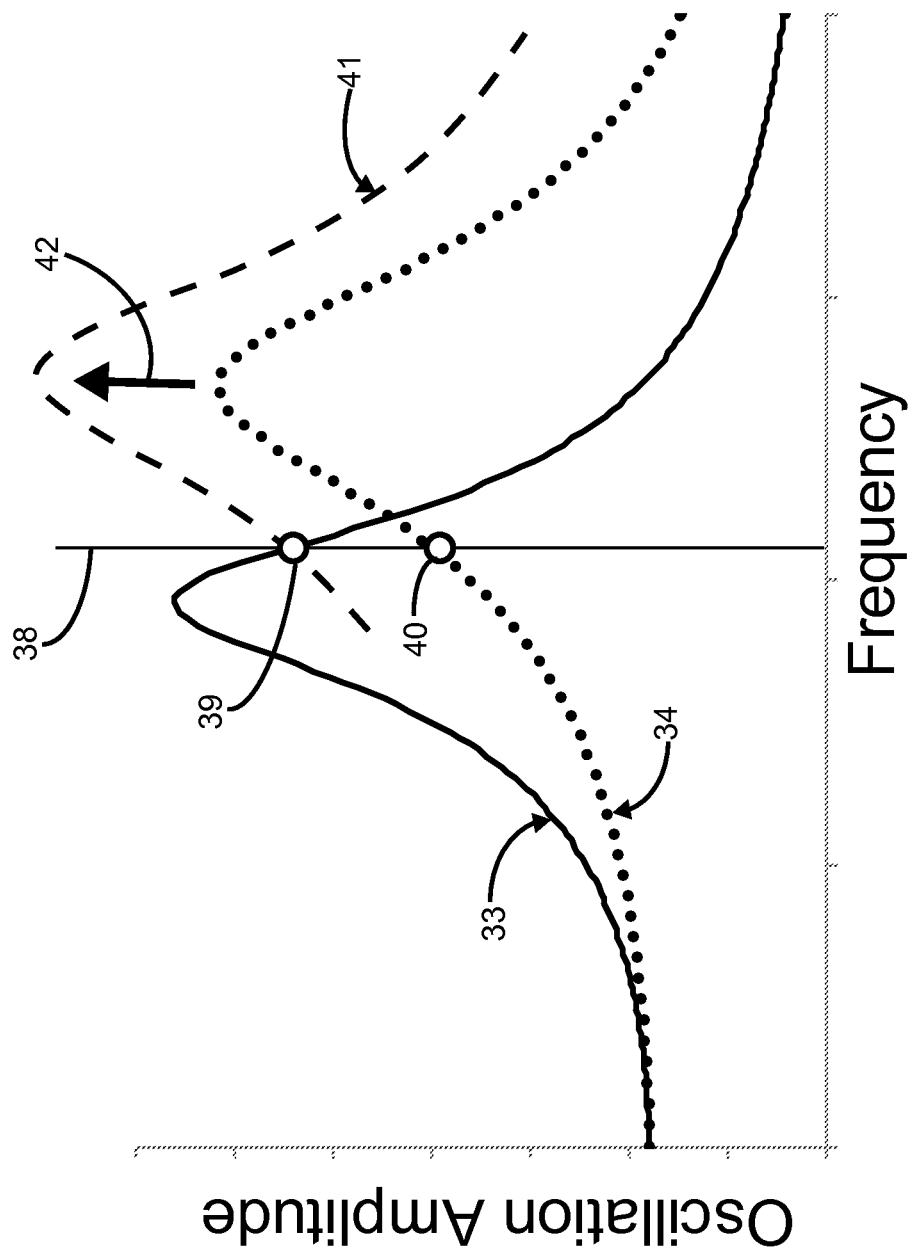
FIG. 10B is a graphic demonstration of a current-based control method for overcoming damping effect of tissue during a tissue penetration event using the driving actuator.

In FIG. 10B, a second method of employing feedback to adjust driving parameters is depicted based on current amplitude control. In this method, current instead of frequency is adjusted during tissue penetration in an attempt to maintain oscillatory displacement levels. As an example, a driving actuator with simulated frequency response in air 33 is driven at the shown operating frequency 38 yielding the oscillatory displacement at operating frequency in air 39. When the penetrating member attached to the driving actuator contacts tissue, the simulated frequency response in tissue 34 may be shifted relative to the simulated frequency response in air 33 as the graph suggests. The shifted simulated frequency response in tissue 34 has reduced displacement at operating frequency after contacting tissue 40 at the operating frequency 38. To counteract the damping of displacement, current amplitude supplied to the driving actuator is increased, resulting in a modified frequency response following increase in current 41, shifted upward as indicated by the arrow 42. Current is increased until the oscillatory displacement reaches the displacement at operating frequency in air 39. At this point the modified frequency response 41 of the coupled system intersects the original simulated frequency response in air 33 at the operating frequency 38, albeit requiring a higher driving current amplitude.

Additional means for maintaining oscillatory displacement level could employ a combination of frequency and current control.

FIG. 11 shows the oscillatory displacement amplitude that was measured during insertions into skin tissue at different operating frequency. The resonant frequency of the driving actuator which was used to obtain these curves was near 95 Hz. When the operating frequency was chosen to coincide with the resonant frequency, the oscillatory displacement is damped considerably as shown in the displacement versus insertion depth plot with operating frequency at 95 Hz 43. Choosing an operating frequency of 120 Hz (25 Hz above resonant frequency), the displacement actually increases as the penetrating member contacted and inserted through tissue as shown in displacement versus insertion depth plot with operating frequency at 120 Hz 44. Choosing an even higher operating frequency, the displacement versus insertion depth plot with operating frequency at 150 Hz 45 remained relatively flat. Note: a smaller starting displacement was chosen for plot 45 as compared to plots 43 and 44. Another notable feature with operating at a frequency above the resonance of non-loaded system is that the displacement tends to increase during penetration as the tissue adds axial force to the tip of the penetrating member as seen in plots 44 and 45. When this axial force is removed or reduced, such as when a vessel wall or tissue plane is penetrated, the displacement may decrease, reducing the risk of over penetration. When a feedback loop is employed to control the displacement (see descriptions of FIGS. 6A and 6B), abrupt changes in the axial force (e.g. penetration through a vessel wall) could be sensed by a change in driving characteristics (e.g. power, phase, resonant frequency, oscillation amplitude) to indicate needle tip location (e.g. entry into vessel lumen).

Figure 12:
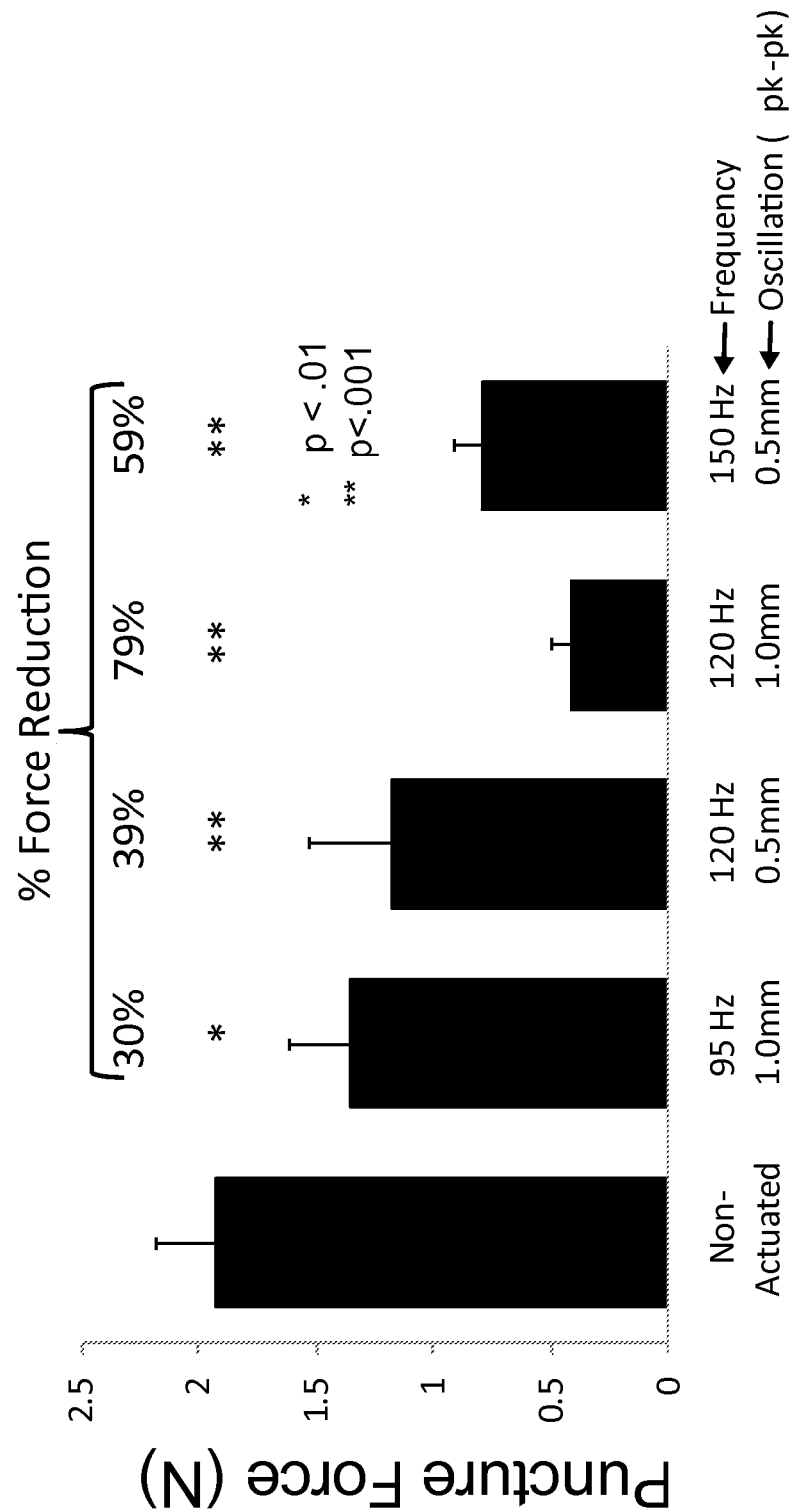
FIG. 12 is a graphical summary of insertion tests of a reciprocated 18G hypodermic needle into porcine skin with the driving actuator delivering different displacement frequency and amplitude levels.

FIG. 12 presents data obtained from insertions into porcine skin with an 18 gauge hypodermic needle serving as the penetrating member. Performance for different operating frequency and starting (in air) oscillatory displacement settings are shown. Depending on the choice of operating parameters, significant force reductions are seen in comparison to insertions of a non-actuated (non-oscillated) needle.

Figure 13:
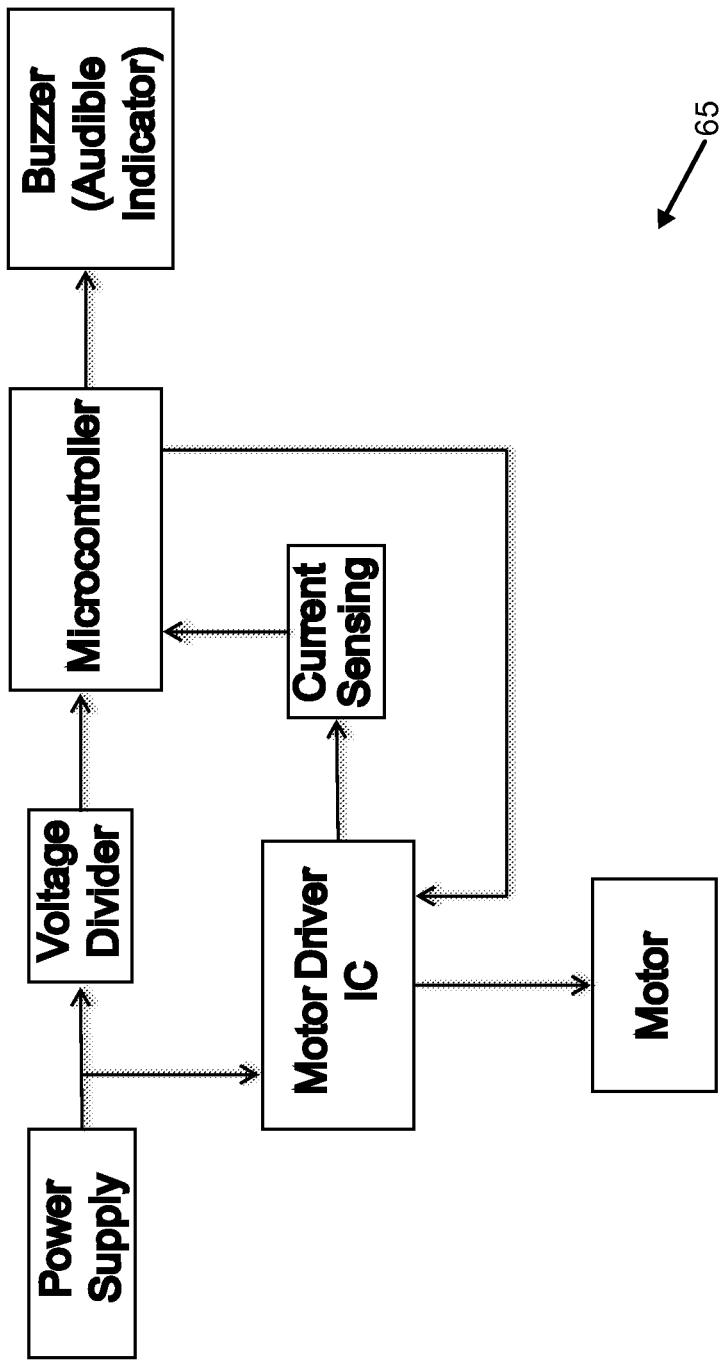
FIG. 13 is a block diagram of electronics layout for voltage and current sensing applications.

FIG. 13 is a control electronics diagram 65 that presents one method of utilizing voltage and current sensing for various control actions. The control electronics employ two sensing methods to ensure that the motor function is operating correctly and to signal the operator if any faults occur. The voltage from the power supply is applied directly to the Motor Driver IC. This voltage is also sensed by the Microcontroller through a Voltage Divider circuit. The Microcontroller monitors this voltage signal and will disable the Motor Driver IC and initiate the Buzzer if the voltage level is outside of a predetermined window. Likewise the Microcontroller also senses and monitors the current through the motor via a current sense pin on the Motor Driver IC. If this current level exceeds a predetermined limit the Microcontroller will disable the Motor Driver IC and initiate the Buzzer. In alternate designs the microcontroller could also be monitoring voltage and current frequency and their relative phase angles.

In the preferred embodiment of the VCM-based driving actuator 1, the VCM coil 2 may be driven by control circuitry such that a constant supply voltage can be applied to the VCM coil 2 at both positive and negative potential or can be turned off to apply zero volts. This supply voltage is switched on and off at a frequency between 10 kHz and 40 kHz where the time that the supply voltage is either 'on' or 'off' can be adjusted. The average voltage seen by the VCM coil 2 over a given switching cycle is proportional to the time the supply voltage is applied. For example, if the supply voltage is applied for 50% of the switching cycle the average voltage seen by the VCM coil 2 will be 50% of the supply voltage. When the VCM coil 2 is supplied with a positive potential voltage a force proportional to the applied voltage will be applied to the magnet assembly 4 of the VCM in one direction while a negative potential voltage will apply a force to the magnet assembly 4 in the opposite direction. By periodically reversing the polarity of the applied potential of the switching signal at 50-500 Hz, an oscillating force can be applied to the motor shaft 5 by way of the attached magnet assembly 4 with an average magnitude proportional to the average voltage magnitude of the generated signal. The energy of this signal will be located at the frequency at which the potential is reversed and every odd multiple of this frequency, the magnitude of which will decrease with each increasing multiple. Likewise, additional energy will also be located at the switching frequency and every odd multiple of this frequency, the magnitude of which will decrease with each increasing multiple.

The frequency response seen in FIGS. 9, 10A and 10B is highly resonant with a weaker response far from the resonant frequency. When the actuator is driven with the described signal where the potential reversal frequency is near resonance, the effects of the energy at higher frequencies is greatly attenuated to the point that they are almost non-existent. This results in a very sinusoidal response without the need for additional filtering or smoothing circuitry. Driving the actuator using this method was chosen because the circuitry necessary to create the signal described is very simple, efficient and cost effective compared to sinusoidal signal generation and is able to take advantage of the physics of the actuator. The ability to use this method is one of the benefits of the VCM design because this method would not be practical to drive an actuator with a wide frequency response when only one frequency of actuation is desired.

Now that exemplary embodiments of the present invention have been shown and described in detail, various modifications and improvements thereon will become apparent. While the foregoing embodiments may have dealt with the penetration through skin, bone, veins and ligaments as exemplary biological tissues, the present invention can undoubtedly ensure similar effects with other tissues which are commonly penetrated within the body. For example there are multiplicities of other tools like central venous catheter introducers, laparoscopic instruments with associated sharps, cavity drainage catheter kits, and neonatal lancets, as well as procedures like insulin administration and percutaneous glucose testing, to name a few, where embodiments disclosed herein comprising sonically or ultrasonically driven sharps members may be used to precisely pierce or puncture tissues with minimal tinting.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

REFERENCE LABELS

1 Driving Actuator
1b Handpiece body
2 Voice Coil
3 Centering Magnet
4 Magnet Assembly
4a Magnet Array
4b Opposite Magnet Array
4c Pole Piece
5 Motor Shaft
5b Motor Shaft Bearing
6 Keyed Coupler
7 Power Cable
8 VCM Body
8b VCM End Cap
9 Power Button
10 Penetrating Member
11 Hub
12 Bevel End
13 Keyway
14 Keys
15 Coupling Piece with Side Port
16 Side Port
17 Compliant Tubing
18 Syringe Body
19 Plunger
20 Syringe Coupling Bracket
21 IV Catheter
22 Coupling Sled
22a Cops
22b Proximal End of Coupling Sled
23 Safety IV Device
24 Not Used
25 Penetrating member (IV Device)
26 Frequency Response of Driving Actuator in Air (non-loaded)
27 Frequency Response of Driving Actuator with Axial Force Applied (loaded)
28 Resonant Frequency in Air
29 Resonant Frequency with 1 N of Axial Force Applied
30 Oscillatory Displacement Damping at Original Resonant Frequency
31 Resonant Frequency Shift
32 Damping Resistant Operating Frequency
33 Simulated Frequency Response in Air
34 Simulated Frequency Response in Tissue
35 Resonant Displacement Peak in Air (simulated)
36 Displacement in Tissue at Original Resonant Frequency (simulated)
37 Resonant Displacement Peak in Tissue (simulated)
38 Operating frequency
39 Displacement at Operating Frequency in Air (simulated)
40 Displacement at Operating Frequency After Contacting Tissue (simulated)
41 Frequency Response Following Increase in Current (simulated)
42 Arrow
43 Displacement versus Insertion Depth Plot with Operating Frequency at 95 Hz
44 Displacement versus Insertion Depth Plot with Operating Frequency at 120 Hz
45 Displacement versus Insertion Depth Plot with Operating Frequency at 150 Hz
46 Attachment Clip
47 Syringe Adapter
48 Syringe View Window
49 Guide Shaft
49a Geared Guide Shaft
50 Guide Shaft Coupling
51 Syringe Coupler
52 Syringe Clip
53 Thumb Coupler
54 Drive Gear
54a Drive Gear Two
54b Idler Gear
55 Drive Gear Housing
56 Slider Device
57 Geared Slider Device
58 Section A-A
59 Section B-B
60 Section C-C
61 Section D-D
62 Foot Switch
63 Forward Position
64 Backward Position
65 Control Electronics Diagram
66 Axis of Rotation
67 Rotating Keyway Head
68 Rotating Motion
69 LVDT
70 LVDT Core
71 Resonant Frequency in Tissue (simulated)

What is claimed:

1. A device for penetrating tissue, comprising:
a driving actuator that has a body and a motor shaft, wherein the motor shaft is reciprocated;
a penetrating member coupled to said motor shaft, wherein reciprocation of the motor shaft is translated to the penetrating member to reciprocate the penetrating member; and
a controller in electrical communication with the driving actuator and configured to send signals to the driving actuator to reciprocate the motor shaft according to a preselected operating frequency based on tissue type to be penetrated, wherein said preselected operating frequency is sufficient to offset at least a portion of damping of oscillatory displacement amplitude resulting from a resonant frequency shift from air to said tissue type upon insertion of said penetrating member into said tissue type, wherein the preselected operating frequency is selected from the group consisting of:
(i) the resonance frequency of the penetrating member in said tissue type;

(ii) a frequency higher than a resonant frequency of said penetrating member in air;
(iii) in the range of ⅓ to ½ octave higher than the resonant frequency of said penetrating member in air; and
(iv) in the range of 95-150 Hz.

2. The device as set forth in claim 1, wherein the controller is configured to perform at least one of the following:
   maintaining the preselected operating frequency during penetration of tissue;
   maintaining a current amplitude to the driving actuator during penetration of tissue;
   increasing a current amplitude to the driving actuator during penetration of tissue.

3. The device as set forth in claim 1, further comprising a keyed coupler that is attached to the motor shaft, wherein the penetrating member is carried by the keyed coupler, wherein the keyed coupler has a key;
   wherein the body of the driving actuator is an exterior handpiece body that defines a keyway, wherein the key is disposed within the keyway, and wherein the key prevents rotational motion of the motor shaft during reciprocation of the motor shaft.

4. The device as set forth in claim 1, wherein the driving actuator has a first magnet array and a second magnet array, and wherein the driving actuator has a first centering magnet and a second centering magnet, wherein the first and second magnet arrays are located between the first and second centering magnets, wherein the first centering magnet and the first magnet array repel one another, and wherein the second centering magnet and the second magnet array repel one another, wherein alternating current is applied to the first and second magnet arrays to cause the first and second magnet arrays to reciprocate, wherein the reciprocation of the first and second magnet arrays is translated to the motor shaft.

5. The device as set forth in claim 1, wherein the preselected operating frequency is the resonance frequency of the penetrating member in tissue.

6. A device as set forth in claim 1, further comprising a coupler attached to the motor shaft for removably affixing a penetrating member to the motor shaft, wherein linear motion of the motor shaft is translated to the penetrating member to linearly reciprocate the penetrating member, said coupler having a key integral to and extending outwardly from the coupler and engaging the driving actuator, limiting rotational motion and permitting linear motion of the motor shaft.

7. The device as set forth in claim 6, wherein the body of the driving actuator is an exterior handpiece body that defines a keyway, wherein the key is disposed within the keyway, wherein the key prevents rotational motion of the motor shaft, and wherein the penetrating member has a beveled end.

8. The device as set forth in claim 6, further comprising:
   a coupling sled selectively attachable to the body of the driving actuator and configured to move relative to the body of the driving actuator during reciprocation of the motor shaft;
   a safety IV device that is releasably attachable to the coupling sled and configured to move relative to the body of the driving actuator during reciprocation of the motor shaft, wherein the penetrating member is carried by the safety IV device so as to be carried by the coupler; and
   an IV catheter located on the penetrating member, wherein the N catheter is removable from the penetrating member, and wherein the penetrating member is retractable into the safety IV device after removal of the IV catheter from the penetrating member.

9. The device as set forth in claim 6, further comprising:
   a syringe clip carried by the coupler, wherein the penetrating member is carried by the syringe dip so as to be carried by the coupler;
   a handpiece dip attached to the body of the driving actuator, wherein the body of the driving actuator is an exterior handpiece body, wherein the handpiece dip has a moveable portion that is movable relative to the body of the driving actuator;
   a syringe carried by the handpiece dip so as to be side mounted to the body of the driving actuator;
   a plunger that is in communication with the moveable portion of the handpiece dip, wherein movement of the moveable portion of the handpiece clip causes movement of the plunger relative to the syringe.

10. The device as set forth in claim 9, wherein the movable portion of the handpiece dip has a drive gear and a guide shaft, wherein the drive gear is rotatable and is in gearing communication with a rack of the guide shaft, wherein rotation of the drive gear causes linear movement of the guide shaft;
    further comprising a guide shaft coupling that is attached to the guide shaft and to the plunger, wherein the plunger is in communication with the guide shaft by way of the guide shaft coupling such that linear movement of the guide shaft causes linear movement of the plunger.

11. The device as set forth in claim 9, wherein the moveable portion has a switch that is actuated by a finger or thumb of a user, wherein the switch is located adjacent the exterior handpiece body of the driving actuator.

12. The device as set forth in claim 6, wherein the driving actuator has a first magnet array and a second magnet array, wherein the first magnet array is located proximal to the second magnet array, wherein the driving actuator has a first centering magnet located proximal to both the first and second magnet arrays, wherein the first centering magnet and the first magnet array repel one another, wherein the driving actuator has a second centering magnet that is located distal to the first centering magnet and the first and second magnet arrays, wherein the second centering magnet and the second magnet array repel one another, wherein alternating current is applied to the first and second magnet arrays by a coil of the driving actuator to cause the first and second magnet arrays to reciprocate, wherein the reciprocation of the first and second magnet arrays is translated to the motor shaft.

13. The device as set forth in claim 12, wherein the driving actuator has a voice coil through which the alternating current is applied to the first and second magnet arrays, wherein the driving actuator has a first end cap that is located proximal to the first centering magnet, wherein the driving actuator has a second end cap that is located distal to the second centering magnet, wherein the driving actuator has a pole piece that is located between the first and second magnet arrays, wherein the motor shaft extends through the first end cap, the first centering magnet, the first magnet array, the pole piece, the second magnet array, the second centering magnet, and the second end cap.

14. The device as set forth in claim 6, wherein the penetrating member has a hub, wherein the hub has an attachment selected from the group consisting of a LUER lock attachment and a slip tip attachment;
    and wherein the coupler is configured to be reversibly attachable to a LUER lock attachment and a slip tip attachment, wherein the hub is attached to the coupler such that the attachment is received by the coupler.

15. The device as set forth in claim 1, wherein the body of the driving actuator is an exterior handpiece body, and wherein the penetrating member has an inner lumen, and further comprising:
a syringe coupling bracket that is releasably attached to the exterior handpiece body;
a syringe body that is releasably attached to the syringe coupling bracket, when an axis of the syringe body is not coaxial with an axis of the penetrating member; and
a plunger that moves relative to the syringe body, wherein fluid in the syringe body is dispensed from the syringe body through a side port and into the inner lumen of the penetrating member.

16. The device as set forth in claim 1, further comprising:
a coupling sled that engages the body of the driving actuator and is configured to move relative to the body of the driving actuator during reciprocation of the motor shaft;
a safety IV device that is releasably attachable to the coupling sled and configured to move relative to the body of the driving actuator during reciprocation of the motor shaft, wherein the penetrating member is carried by the safety IV device; and
an IV catheter located on the penetrating member, wherein the IV catheter is removable from the penetrating member, and wherein the penetrating member Is retractable into the safety IV device after removal of the IV catheter from the penetrating member.

17. The device as set forth in claim 1, further comprising a keyed coupler that is attached to the motor shaft, wherein the penetrating member is carried by the keyed coupler, wherein the keyed coupler has a key;
wherein the body of the driving actuator is an exterior handpiece body that defines a keyway, wherein the key is disposed within the keyway, and wherein the key prevents rotational motion of the motor shaft during reciprocation of the motor shaft.

18. The device as set forth in claim 1, wherein said preselected operating frequency is a frequency higher than a resonant frequency of said penetrating member in air.

19. The device as set forth in claim 1, wherein said preselected operating frequency is in the range of ⅓ to ½ octave higher than the resonant frequency of said penetrating member in air.

20. The device as set forth in claim 1, wherein said preselected operating frequency is in the range of 95-150 Hz.

21. The device as set forth in claim 1, wherein:
the driving actuator has a first magnet array and a second magnet array, and wherein the driving actuator has a first centering magnet and a second centering magnet, wherein the first and second magnet arrays are located between the first and second centering magnets, wherein the first centering magnet and the first magnet array repel one another, and wherein the second centering magnet and the second magnet array repel one another, wherein alternating current is applied to the first and second magnet arrays to cause the first and second magnet arrays to reciprocate, wherein the reciprocation of the first and second magnet arrays is translated to the motor shaft.

22. The device as set forth in claim 1, wherein said preselected operating frequency Is an initial operating frequency and said controller is configured to send signals to the driving actuator to reciprocate the motor shaft according to a technique selected from the group consisting of:
(a) driving the motor shaft at said preselected operating frequency when penetrating tissue;
(b) driving the motor shaft at the said preselected operating frequency and providing a constant current amplitude to the driving actuator when penetrating tissue;
(c) driving the motor shaft at the said preselected operating frequency and increasing said current amplitude when penetrating tissue; and
(d) driving the motor shaft by increasing said current amplitude and a subsequent operating frequency that differs from said preselected operating frequency when penetrating tissue.

23. The device as set forth in claim 22, further comprising a displacement sensor configured to monitor oscillatory displacement amplitude during reciprocation of said penetrating member, wherein a feedback loop is employed and configured to use Input from the displacement sensor to optimize performance of the device by adjusting a property of the device selected from the group consisting of:
the initial operating frequency of the driving actuator such that the subsequent operating frequency is closer to resonance frequency of said penetrating member in tissue than the initial operating frequency;
current amplitude supplied to the driving actuator during load when penetrating tissue; and
a combination of the initial operating frequency and current amplitude supplied to the driving actuator.

24. A device for penetrating tissue, comprising:
a driving actuator having:
(i) an exterior handpiece body;
(ii) a motor shaft configured to be reciprocated;
(iii) a first magnet array and a second magnet array, the first magnet array located proximal to the second magnet array;
(iv) a first centering magnet located proximal to both the first and second magnet arrays, the first centering magnet and the first magnet array configured to repel one another;
(v) a second centering magnet located distal to the first centering magnet and the first and second magnet arrays, the second centering magnet and the second magnet array configured to repel one another; and
(vi) a coil;
the first and second magnet arrays configured to receive alternating current from the coil of the driving actuator, reciprocate, and translate the reciprocation to the motor shaft;
a penetrating member having an inner lumen and a penetrating axis defined along its length, the penetrating member removably affixed to the motor shaft and receiving reciprocation from the motor shaft;
a coupler attached to the motor shaft, the coupler removably affixing the penetrating member to the motor shaft and configured to translate linear motion from the motor shaft to the penetrating member, the coupler having a key integral to and extending outwardly therefrom, the key engaging the driving actuator, limiting rotational motion and permitting linear motion to the motor shaft;
a controller in electrical communication with the driving actuator and configured to send signals to the driving actuator to reciprocate the motor shaft according to a preselected operating frequency based on the tissue type to be penetrated, the preselected operating frequency being sufficient to offset at least a portion of damping of oscillatory displacement amplitude resulting from a resonant frequency shift from air to tissue upon insertion of the penetrating member into the tissue type;

a syringe coupling bracket configured to releasably attach to the exterior handpiece body;

a syringe body having a syringe axis defined along its length, the syringe body configured to releasably attach to the syringe coupling bracket, the syringe axis being spaced apart form the penetrating axis; and a plunger configured to move relative to the syringe body, wherein fluid in the syringe body is dispensed through a side port into the inner lumen of the penetrating member.

25. The device as set forth in claim 24, wherein the exterior handpiece body defines a keyway, wherein the key is disposed within the keyway, wherein the key prevents rotational motion of the motor shaft, and wherein the penetrating member has a beveled end.

26. The device as set forth in claim 24, wherein said preselected operating frequency is an initial operating frequency and said controller is configured to send signals to the driving actuator to reciprocate the motor shaft according to a technique selected from the group consisting of:
   (a) driving the motor shaft at said preselected operating frequency when penetrating tissue;
   (b) driving the motor shaft at the said preselected operating frequency and providing a constant current amplitude to the driving actuator when penetrating tissue;
   (c) driving the motor shaft at the said preselected operating frequency and increasing said current amplitude when penetrating tissue; and
   (d) driving the motor shaft by increasing said current amplitude and a subsequent operating frequency that differs from said preselected operating frequency when penetrating tissue.

27. The device as set forth in claim 26, further comprising a displacement sensor configured to monitor oscillatory displacement amplitude during reciprocation of said penetrating member, wherein a feedback loop is employed and configured to use input from the displacement sensor to optimize performance of the device by adjusting a property of the device selected from the group consisting of:
   the initial operating frequency of the driving actuator such that the subsequent operating frequency is closer to resonance frequency of said penetrating member in tissue than the initial operating frequency;
   current amplitude supplied to the driving actuator during load when penetrating tissue; and
   a combination of the initial operating frequency and current amplitude supplied to the driving actuator.

28. The device as set forth in claim 24, wherein the penetrating member has a hub, wherein the hub has an attachment selected from the group consisting of a LUER lock attachment and a slip tip attachment;
   and wherein the coupler is configured to be reversibly attachable to a LUER lock attachment and a slip tip attachment, wherein the hub is attached to the coupler such that the attachment is received by the coupler.

29. The device as set forth in claim 24, wherein the controller is configured to perform at least one of the following:
   maintaining the preselected operating frequency during penetration of tissue;
   maintaining a current amplitude to the driving actuator during penetration of tissue;
   increasing a current amplitude to the drying actuator during penetration of tissue.

30. The device as set forth in claim 24, wherein the preselected operating frequency is selected from the group consisting of:
   (i) the resonance frequency of the penetrating member in tissue;
   (ii) a frequency higher than a resonant frequency of said penetrating member in air;
   (iii) in the range of ⅓ to ½ octave higher than the resonant frequency of said penetrating member in air; and
   (iv) in the range of 95-150 Hz.

31. The device as set forth in claim 24, wherein the driving actuator has a voice coil through which the alternating current is applied to the first and second magnet arrays, wherein the driving actuator has a first end cap that is located proximal to the first centering magnet, wherein the driving actuator has a second end cap that is located distal to the second centering magnet, wherein the driving actuator has a pole piece that is located between the first and second magnet arrays, wherein the motor shaft extends through the first end cap, the first centering magnet, the first magnet array, the pole piece, the second magnet array, the second centering magnet, and the second end cap.

32. The device as set forth in claim 24, further comprising:
   a coupling sled selectively attachable to the body of the driving actuator and configured to move relative to the body of the driving actuator during reciprocation of the motor shaft;
   a safety IV device that is releasably attachable to the coupling sled and configured to move relative to the body of the driving actuator during reciprocation of the motor shaft, wherein the penetrating member is carried by the safety IV device so as to be carried by the coupler; and
   an IV catheter located on the penetrating member, wherein the IV catheter is removable from the penetrating member, and wherein the penetrating member is retractable into the safety IV device after removal of the IV catheter from the penetrating member.

33. The device as set forth in claim 24, further comprising:
   a syringe clip carried by the coupler, wherein the penetrating member is carried by the syringe clip so as to be carried by the coupler;
   a handpiece clip attached to the exterior handpiece body, wherein the handpiece clip has a moveable portion that is movable relative to the body of the driving actuator;
   a syringe carried by the handpiece clip so as to be side mounted to the body of the driving actuator;
   wherein the plunger is in communication with the moveable portion of the handpiece clip and movement of the moveable portion of the handpiece clip causes movement of the plunger relative to the syringe.

34. The device as set forth in claim 33, wherein the moveable portion of the handpiece clip has a drive gear and a guide shaft, wherein the drive gear is rotatable and is in gearing communication with a rack of the guide shaft, wherein rotation of the drive gear causes linear movement of the guide shaft;
   further comprising a guide shaft coupling that is attached to the guide shaft and to the plunger, wherein the plunger is in communication with the guide shaft by way of the guide shaft coupling such that linear movement of the guide shaft causes linear movement of the plunger.

35. The device as set forth in claim 33, wherein the moveable portion has a switch that is actuated by a finger or thumb of a user, wherein the switch is located adjacent the exterior handpiece body of the driving actuator.

* * * * *